(12) United States Patent
Lipkens et al.

(10) Patent No.: US 11,708,572 B2
(45) Date of Patent: Jul. 25, 2023

(54) ACOUSTIC CELL SEPARATION TECHNIQUES AND PROCESSES

(71) Applicant: FloDesign Sonics, Inc., West Springfield, MA (US)

(72) Inventors: Bart Lipkens, Bloomfield, CT (US); Kedar C. Chitale, Vernon, CT (US); Krishna N. Kumar, Wilbraham, MA (US); Walter M. Presz, Jr., Wilbraham, MA (US); Ruan Zhang, Winchester, MA (US); Benjamin Ross-Johnsrud, Northampton, MA (US); Rudolf Gilmanshin, Framingham, MA (US); Natalia Rodionova, Framingham, MA (US); Rui Tostoes, Northampton, MA (US)

(73) Assignee: FloDesign Sonics, Inc., West Springfield, MA (US)

(*) Notice: Subject to any disclaimer, the term of this patent is extended or adjusted under 35 U.S.C. 154(b) by 614 days.

(21) Appl. No.: 16/421,459

(22) Filed: May 23, 2019

(65) Prior Publication Data

US 2019/0345477 A1  Nov. 14, 2019

Related U.S. Application Data

(63) Continuation-in-part of application No. 16/010,296, filed on Jun. 15, 2018, and a continuation-in-part of application No. 15/942,316, filed on Mar. 30, 2018, now Pat. No. 11,021,699, said application No. 16/010,296 is a continuation-in-part of application No. 15/916,270, filed on Mar. 8, 2018, now Pat. No. 11,377,651, application No. 16/421,459 is a continuation-in-part of application No. 15/788,784, filed on Oct. 19, 2017, now Pat. No. 11,420,136, said application No. 15/942,316 is a continuation-in-part of application No. 15/613,790, filed on Jun. 5, 2017, now Pat. No. 10,550,382, application No. 16/421,459 is a continuation-in-part of application No. 15/586,116, filed on May 3, 2017, now Pat. No. 10,640,760, said application No. 15/613,790 is a continuation of application No. 15/143,481, filed on Apr. 29, 2016, now Pat. No. 9,670,477.

(60) Provisional application No. 62/679,012, filed on May 31, 2018, provisional application No. 62/675,194, filed on May 23, 2018, provisional application No. 62/520,488, filed on Jun. 15, 2017, provisional application No. 62/485,229, filed on Apr. 13, 2017, (Continued)

(51) Int. Cl.
| | | |
|---|---|---|
| *C12N 13/00* | (2006.01) | |
| *B01D 21/28* | (2006.01) | |
| *G01N 15/14* | (2006.01) | |
| *A61M 1/36* | (2006.01) | |
| *B01L 3/00* | (2006.01) | |
| *C12M 1/00* | (2006.01) | |
| *G01N 15/00* | (2006.01) | |
| *G01N 15/10* | (2006.01) | |

(52) U.S. Cl.
CPC .......... *C12N 13/00* (2013.01); *A61M 1/3678* (2014.02); *B01D 21/283* (2013.01); *B01L 3/502761* (2013.01); *C12M 47/04* (2013.01); *G01N 15/1484* (2013.01); *B01L 2300/0864* (2013.01); *B01L 2300/0867* (2013.01); *B01L 2400/0436* (2013.01); *B01L 2400/0439* (2013.01); *G01N 2015/0053* (2013.01); *G01N 2015/1006* (2013.01); *G01N 2015/149* (2013.01)

(58) Field of Classification Search
CPC . A61M 1/3618; A61M 1/3678; B01D 21/283; B01L 2200/0652; B01L 2300/0864; B01L 2300/0867; B01L 2400/0436; B01L 2400/0439; B01L 3/50273; B01L 3/502761; C12M 47/04; C12N 13/00; G01N 15/1484; G01N 2015/0053; G01N 2015/1006; G01N 2015/149
See application file for complete search history.

(56) References Cited

U.S. PATENT DOCUMENTS

| | | |
|---|---|---|
| 2,473,971 A | 6/1949 | Ross |
| 2,667,944 A | 2/1954 | Crites |

(Continued)

FOREIGN PATENT DOCUMENTS

| | | |
|---|---|---|
| AU | 2002236405 | 9/2002 |
| CN | 1337580 A | 2/2002 |

(Continued)

OTHER PUBLICATIONS

Lenshof et al., "Efficient Purification of CD4+ Lymphocytes from Peripheral Blood Progenitor Cell Products Using Affinity Bead Acoustophoresis", Cytometry Part A, 85A, 2014, pp. 933-941.

(Continued)

*Primary Examiner* — Blaine Lankford
(74) *Attorney, Agent, or Firm* — FloDesign Sonics, Inc.

(57) ABSTRACT

Beads with functionalized material applied to them are exposed to an acoustic field to trap, retain or pass the beads. The beads may include or be free of ferro magnetic material. The beads may be biocompatible or biodegradable for a host. The size of the beads may vary over a range, and/or be heterogenous or homogenous. The composition of the beads may include high, neutral or low acoustic contrast material. The chemistry of the functionalized material may be compatible with existing processes. The acoustic field may be generated, for example, in an acoustic angled wave device or in an acoustic fluidized bed.

14 Claims, 16 Drawing Sheets

Related U.S. Application Data provisional application No. 62/479,309, filed on Mar. 30, 2017, provisional application No. 62/468,895, filed on Mar. 8, 2017, provisional application No. 62/410,312, filed on Oct. 19, 2016, provisional application No. 62/374,910, filed on Aug. 15, 2016, provisional application No. 62/359,182, filed on Jul. 6, 2016, provisional application No. 62/330,947, filed on May 3, 2016, provisional application No. 62/316,933, filed on Apr. 1, 2016, provisional application No. 62/154,690, filed on Apr. 29, 2015.

(56) References Cited

U.S. PATENT DOCUMENTS

| | | | |
|---|---|---|---|
| 3,372,370 | A | 3/1968 | Cyr |
| 3,555,311 | A | 1/1971 | Weber |
| 4,055,491 | A | 10/1977 | Porath-Furedi |
| 4,065,875 | A | 1/1978 | Srna |
| 4,118,649 | A | 10/1978 | Schwartzman et al. |
| 4,125,789 | A | 11/1978 | Van Schoiack |
| 4,158,629 | A | 6/1979 | Sawyer |
| 4,165,273 | A | 8/1979 | Azarov et al. |
| 4,173,725 | A | 11/1979 | Asai et al. |
| 4,204,096 | A | 5/1980 | Barcus et al. |
| 4,211,949 | A | 7/1980 | Brisken |
| 4,254,661 | A | 3/1981 | Kossoff et al. |
| 4,320,659 | A | 3/1982 | Lynnworth et al. |
| 4,344,448 | A | 8/1982 | Potts |
| 4,398,325 | A | 8/1983 | Piaget et al. |
| 4,484,907 | A | 11/1984 | Sheeran, Jr. |
| 4,552,669 | A | 11/1985 | Sekellick |
| 4,666,595 | A | 5/1987 | Graham |
| 4,673,512 | A | 6/1987 | Schram |
| 4,699,588 | A | 10/1987 | Zinn et al. |
| 4,743,361 | A | 5/1988 | Schram |
| 4,759,775 | A | 7/1988 | Peterson et al. |
| 4,800,316 | A | 1/1989 | Wang |
| 4,821,838 | A | 4/1989 | Chen |
| 4,836,684 | A | 6/1989 | Javorik et al. |
| 4,860,993 | A | 8/1989 | Goode |
| 4,878,210 | A | 10/1989 | Mitome |
| 4,983,189 | A | 1/1991 | Peterson et al. |
| 5,002,890 | A | 3/1991 | Morrison |
| 5,059,811 | A | 10/1991 | King et al. |
| 5,062,965 | A | 11/1991 | Bernou et al. |
| 5,085,783 | A | 2/1992 | Feke et al. |
| 5,164,094 | A | 11/1992 | Stuckart |
| 5,225,089 | A | 7/1993 | Benes et al. |
| 5,371,429 | A | 12/1994 | Manna |
| 5,395,592 | A | 3/1995 | Bolleman et al. |
| 5,431,817 | A | 7/1995 | Braatz et al. |
| 5,443,985 | A | 8/1995 | Lu et al. |
| 5,452,267 | A | 9/1995 | Spevak |
| 5,475,486 | A | 12/1995 | Paoli |
| 5,484,537 | A | 1/1996 | Whitworth |
| 5,527,460 | A | 6/1996 | Trampler et al. |
| 5,560,362 | A | 10/1996 | Sliwa, Jr. et al. |
| 5,562,823 | A | 10/1996 | Reeves |
| 5,594,165 | A | 1/1997 | Madanshetty |
| 5,604,301 | A | 2/1997 | Mountford et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,779,911 | A | 7/1998 | Haug et al. |
| 5,831,166 | A | 11/1998 | Kozuka et al. |
| 5,834,871 | A | 11/1998 | Puskas |
| 5,844,140 | A | 12/1998 | Seale |
| 5,902,489 | A | 5/1999 | Yasuda et al. |
| 5,912,182 | A | 6/1999 | Coakley et al. |
| 5,947,299 | A | 9/1999 | Vazquez et al. |
| 5,951,456 | A | 9/1999 | Scott |
| 6,029,518 | A | 2/2000 | Oeftering |
| 6,090,295 | A | 6/2000 | Raghavarao et al. |
| 6,161,435 | A | 12/2000 | Bond et al. |
| 6,166,231 | A | 12/2000 | Hoeksema |
| 6,216,538 | B1 | 4/2001 | Yasuda et al. |
| 6,205,848 | B1 | 6/2001 | Faber et al. |
| 6,273,262 | B1 | 8/2001 | Yasuda et al. |
| 6,286,370 | B1 | 9/2001 | Sinha |
| 6,332,541 | B1 | 12/2001 | Coakley et al. |
| 6,391,653 | B1 | 5/2002 | Letcher et al. |
| 6,475,151 | B2 | 11/2002 | Koger et al. |
| 6,482,327 | B1 | 11/2002 | Mori et al. |
| 6,487,095 | B1 | 11/2002 | Malik et al. |
| 6,592,821 | B1 | 7/2003 | Wada et al. |
| 6,641,708 | B1 | 11/2003 | Becker et al. |
| 6,649,069 | B2 | 11/2003 | DeAngelis |
| 6,699,711 | B1 | 3/2004 | Hahn et al. |
| 6,727,451 | B1 | 4/2004 | Fuhr et al. |
| 6,763,722 | B2 | 7/2004 | Fjield et al. |
| 6,881,314 | B1 | 4/2005 | Wang et al. |
| 6,929,750 | B2 | 8/2005 | Laurell et al. |
| 6,936,151 | B1 | 8/2005 | Lock et al. |
| 7,008,540 | B1 | 3/2006 | Weavers et al. |
| 7,010,979 | B2 | 3/2006 | Scott |
| 7,061,163 | B2 | 6/2006 | Nagahara et al. |
| 7,081,192 | B1* | 7/2006 | Wang .................. B03C 5/028 422/68.1 |
| 7,093,482 | B2 | 8/2006 | Berndt |
| 7,108,137 | B2 | 9/2006 | Lal et al. |
| 7,150,779 | B2 | 12/2006 | Meegan, Jr. |
| 7,186,502 | B2 | 3/2007 | Vesey |
| 7,191,787 | B1 | 3/2007 | Redeker et al. |
| 7,235,227 | B2 | 6/2007 | Lanza et al. |
| 7,322,431 | B2 | 1/2008 | Ratcliff |
| 7,331,233 | B2 | 2/2008 | Scott |
| 7,340,957 | B2 | 3/2008 | Kaduchak et al. |
| 7,373,805 | B2 | 5/2008 | Hawkes et al. |
| 7,541,166 | B2 | 6/2009 | Belgrader et al. |
| 7,601,267 | B2 | 10/2009 | Haake et al. |
| 7,673,516 | B2 | 3/2010 | Janssen et al. |
| 7,674,630 | B2 | 3/2010 | Siversson |
| 7,837,040 | B2 | 11/2010 | Ward et al. |
| 7,846,382 | B2 | 12/2010 | Strand et al. |
| 7,968,049 | B2 | 6/2011 | Takahashi et al. |
| 8,075,786 | B2 | 12/2011 | Bagajewicz |
| 8,080,202 | B2 | 12/2011 | Takahashi et al. |
| 8,134,705 | B2 | 3/2012 | Kaduchak et al. |
| 8,256,076 | B1 | 9/2012 | Feller |
| 8,263,407 | B2 | 9/2012 | Goddard et al. |
| 8,266,950 | B2 | 9/2012 | Kaduchak et al. |
| 8,273,253 | B2 | 9/2012 | Curran |
| 8,273,302 | B2 | 9/2012 | Takahashi et al. |
| 8,309,408 | B2 | 11/2012 | Ward et al. |
| 8,319,398 | B2 | 11/2012 | Vivek et al. |
| 8,334,133 | B2 | 12/2012 | Fedorov et al. |
| 8,387,803 | B2 | 3/2013 | Thorslund et al. |
| 8,592,204 | B2 | 11/2013 | Lipkens et al. |
| 8,679,338 | B2 | 3/2014 | Rietman et al. |
| 8,691,145 | B2 | 4/2014 | Dionne et al. |
| 8,865,003 | B2 | 10/2014 | Yang |
| 8,873,051 | B2 | 10/2014 | Kaduchak et al. |
| 8,889,388 | B2 | 11/2014 | Wang et al. |
| 9,023,658 | B2 | 5/2015 | Gauer et al. |
| 9,272,234 | B2 | 3/2016 | Lipkens et al. |
| 9,357,293 | B2 | 5/2016 | Claussen |
| 9,365,815 | B2 | 6/2016 | Miyazaki et al. |
| 9,368,110 | B1 | 6/2016 | Hershey et al. |
| 9,375,662 | B2 | 6/2016 | Kambayashi et al. |
| 9,388,363 | B2 | 7/2016 | Goodson et al. |
| 9,391,542 | B2 | 7/2016 | Wischnewskiy |
| 9,403,114 | B2 | 8/2016 | Kusuura |
| 9,410,256 | B2 | 8/2016 | Dionne et al. |
| 9,416,344 | B2 | 8/2016 | Lipkens et al. |
| 9,421,553 | B2 | 8/2016 | Dionne et al. |
| 9,422,328 | B2 | 8/2016 | Kennedy, III et al. |
| 9,457,139 | B2 | 10/2016 | Ward et al. |
| 9,457,302 | B2 | 10/2016 | Lipkens et al. |
| 9,458,450 | B2 | 10/2016 | Lipkens et al. |
| 9,464,303 | B2 | 10/2016 | Burke |
| 9,476,855 | B2 | 10/2016 | Ward et al. |
| 9,480,375 | B2 | 11/2016 | Marshall et al. |
| 9,480,935 | B2 | 11/2016 | Mariella, Jr. et al. |

(56) References Cited

U.S. PATENT DOCUMENTS

| | | |
|---|---|---|
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 * | 6/2017 | Lipkens ............ B01L 3/502761 |
| 9,670,938 B2 | 6/2017 | Beliaysky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,718,708 B2 | 8/2017 | LoRicco et al. |
| 9,810,665 B2 | 11/2017 | Fernald et al. |
| 9,833,763 B2 | 12/2017 | Fernald et al. |
| 9,869,618 B2 | 1/2018 | Hoyos |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehlt et al. |
| 9,944,702 B2 | 4/2018 | Galetto |
| 9,944,709 B2 | 4/2018 | Galetto |
| 9,994,743 B2 | 4/2018 | El-Zahab |
| 9,974,898 B2 | 5/2018 | Spain et al. |
| 9,983,459 B2 | 5/2018 | Arnold |
| 10,006,052 B2 | 6/2018 | Jarjour |
| 10,045,913 B2 | 8/2018 | Warner |
| 10,046,028 B2 | 8/2018 | Gregory |
| 10,046,037 B2 | 8/2018 | Weinschenk et al. |
| 10,047,116 B2 | 8/2018 | Morein |
| 10,047,123 B2 | 8/2018 | Weinschenk et al. |
| 10,047,124 B2 | 8/2018 | Weinschenk et al. |
| 10,047,144 B2 | 8/2018 | Elson et al. |
| 10,047,365 B2 | 8/2018 | Williams |
| 10,047,451 B2 | 8/2018 | Gaben |
| 10,047,650 B2 | 8/2018 | Abram |
| 10,052,427 B2 | 8/2018 | Fleig |
| 10,052,431 B2 | 8/2018 | Dreschel |
| 10,052,631 B2 | 8/2018 | Ben-Yakar et al. |
| 10,071,148 B2 | 9/2018 | Weinschenk |
| 10,071,383 B2 | 9/2018 | Dionne |
| 10,072,062 B2 | 9/2018 | Collingwood |
| 10,073,098 B2 | 9/2018 | Wong |
| 10,076,574 B2 | 9/2018 | Wang |
| 10,087,423 B2 | 10/2018 | Wehnes et al. |
| 10,160,786 B1 | 12/2018 | Weinschenk et al. |
| 1,016,731 A1 | 1/2019 | Stickel et al. |
| 1,017,524 A1 | 1/2019 | Lavinder et al. |
| 10,166,255 B2 | 1/2019 | Moriarty et al. |
| 10,166,323 B2 | 1/2019 | Fiering et al. |
| 10,167,474 B2 | 1/2019 | Rossi et al. |
| 10,167,478 B2 | 1/2019 | Wiliams James A |
| 10,190,113 B2 | 1/2019 | Forsyth |
| 10,190,137 B2 | 1/2019 | Zhang et al. |
| 10,195,605 B2 | 2/2019 | Reinbigler |
| 10,196,608 B2 | 2/2019 | Poirot |
| 10,196,651 B2 | 2/2019 | Conway et al. |
| 10,196,652 B2 | 2/2019 | Conway et al. |
| 10,201,365 B2 | 2/2019 | Boudreaux et al. |
| 10,201,652 B2 | 2/2019 | Dutra et al. |
| 10,202,457 B2 | 2/2019 | Ruiz-Opazo et al. |
| 10,202,762 B2 | 2/2019 | Sollohub |
| 10,208,300 B2 | 2/2019 | Messina et al. |
| 10,214,013 B2 | 2/2019 | Foresti et al. |
| 10,214,718 B2 | 2/2019 | Berteau et al. |
| 10,215,760 B2 | 2/2019 | Grove |
| 10,221,843 B2 | 3/2019 | Locker |
| 10,224,015 B2 | 3/2019 | Hsu |
| 10,236,797 B2 | 3/2019 | Wischnewskiy |
| 10,238,365 B2 | 3/2019 | Shiraishi |
| 10,238,741 B2 | 3/2019 | Creusot |
| 10,239,058 B2 | 3/2019 | Lavieu et al. |
| 10,239,948 B2 | 3/2019 | Jullerat et al. |
| 10,245,064 B2 | 4/2019 | Rhee et al. |
| 10,251,664 B2 | 4/2019 | Shelton et al. |
| 10,253,296 B2 | 4/2019 | Kahvejian et al. |
| 10,254,212 B2 | 4/2019 | Ward |
| 10,254,401 B2 | 4/2019 | Suyama |
| 10,258,698 B2 | 4/2019 | Hoge et al. |
| 10,261,078 B2 | 4/2019 | Branch |
| 10,272,163 B2 | 4/2019 | Laterza |
| 10,272,412 B2 | 4/2019 | Rubio Martinez et al. |
| 10,273,283 B2 | 4/2019 | Springer et al. |
| 10,286,007 B2 | 5/2019 | Galetto et al. |
| 10,308,928 B2 | 6/2019 | Lipkens et al. |
| 10,316,063 B1 | 6/2019 | Weinschenk et al. |
| 10,316,101 B2 | 6/2019 | Galetto et al. |
| 10,322,949 B2 | 6/2019 | Lipkens et al. |
| 10,323,065 B1 | 6/2019 | Weinschenk et al. |
| 10,323,076 B2 | 6/2019 | Ellsworth et al. |
| 10,324,082 B2 | 6/2019 | Taylor et al. |
| 10,326,383 B2 | 6/2019 | Stiebel et al. |
| 10,329,531 B2 | 6/2019 | Kahvejian et al. |
| 10,334,390 B2 | 6/2019 | Baskish |
| 1,035,754 A1 | 7/2019 | Fritsche et al. |
| 10,342,829 B2 | 7/2019 | Smith et al. |
| 10,343,187 B2 | 7/2019 | Doyle et al. |
| 10,344,051 B2 | 7/2019 | Bracewell et al. |
| 10,344,263 B2 | 7/2019 | Kahvejian et al. |
| 10,350,514 B2 | 7/2019 | Lipkens et al. |
| 10,357,766 B2 | 7/2019 | Raghen et al. |
| 10,363,496 B2 | 7/2019 | Coutard |

(56) References Cited

U.S. PATENT DOCUMENTS

| | | |
|---|---|---|
| 10,364,271 B2 | 7/2019 | Walz et al. |
| 10,365,191 B2 | 7/2019 | Broyer et al. |
| 10,365,209 B1 | 7/2019 | Beaudoin et al. |
| 10,370,635 B2 | 8/2019 | Lipkens et al. |
| 10,375,508 B2 | 8/2019 | Crockett et al. |
| 10,376,885 B2 | 8/2019 | Cheng et al. |
| 10,378,026 B2 | 8/2019 | Scharenberg et al. |
| 10,381,955 B2 | 8/2019 | Wischnewskiy et al. |
| 10,383,331 B2 | 8/2019 | Ayares |
| 10,550,382 B2 * | 2/2020 | Lipkens ............ B01L 3/502761 |
| 10,640,760 B2 * | 5/2020 | Lipkens ................. C12N 13/00 |
| 11,420,136 B2 | 8/2022 | Lipkens et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Jona Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0055136 A1 | 3/2005 | Hoffman |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0035568 A1 | 2/2008 | Huang et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0033922 A1 | 2/2011 | Landers et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0322692 A1 | 12/2012 | Pham et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115588 A1 | 5/2013 | Davis |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0309757 A1 | 11/2013 | Sung-Chun Kim |
| 2014/0011240 A1 | 1/2014 | Lipkens et al. |
| 2014/0017758 A1 | 1/2014 | Kniep et al. |
| 2014/0033808 A1 | 2/2014 | Ding et al. |
| 2014/0046181 A1 | 2/2014 | Benchimol et al. |
| 2014/0102947 A1 | 4/2014 | Baym et al. |
| 2014/0141413 A1 | 5/2014 | Laugharn, Jr. et al. |
| 2014/0154795 A1 | 6/2014 | Lipkens et al. |
| 2014/0230912 A1 | 8/2014 | Aider et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0253226 A1 * | 9/2015 | Augustsson ..... G01N 33/56972 435/7.25 |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |

(56) References Cited

U.S. PATENT DOCUMENTS

| | | |
|---|---|---|
| 2016/0287778 A1 | 10/2016 | Leach et al. |
| 2016/0312168 A1 | 10/2016 | Pizzi |
| 2016/0314868 A1 | 10/2016 | Ei-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0291122 A1 | 10/2017 | Lipkens et al. |
| 2017/0298316 A1 | 10/2017 | Kennedy et al. |
| 2017/0369865 A1 | 12/2017 | Lipkens et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0143138 A1 | 5/2018 | Shreve et al. |
| 2018/0143167 A1 | 5/2018 | Mziray et al. |
| 2018/0147245 A1 | 5/2018 | O'Shea et al. |
| 2018/0147576 A1 | 5/2018 | Lavieu et al. |

(56) References Cited

U.S. PATENT DOCUMENTS

| | | |
|---|---|---|
| 2018/0148740 A1 | 5/2018 | Conway et al. |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha |
| 2018/0223256 A1 | 8/2018 | Kim |
| 2018/0223273 A1 | 8/2018 | Lipkens |
| 2018/0223439 A1 | 8/2018 | Lipkens |
| 2018/0230433 A1 | 8/2018 | Kokkaliaris |
| 2018/0231555 A1 | 8/2018 | Davis |
| 2018/0236103 A1 | 8/2018 | Friedland |
| 2018/0236280 A1 | 8/2018 | Lipkens Bart et al. |
| 2018/0237533 A1 | 8/2018 | Juillerat et al. |
| 2018/0237768 A1 | 8/2018 | Reik |
| 2018/0237798 A1 | 8/2018 | Duchateau et al. |
| 2018/0243382 A1 | 8/2018 | Wang |
| 2018/0243665 A1 | 8/2018 | Lacki |
| 2018/0244722 A1 | 8/2018 | Stickel |
| 2018/0246103 A1 | 8/2018 | Lipkens |
| 2018/0249688 A1 | 9/2018 | Ayares |
| 2018/0250424 A1 | 9/2018 | Cotta-Ramusino |
| 2018/0251723 A1 | 9/2018 | Murthy |
| 2018/0251770 A1 | 9/2018 | Friedland |
| 2018/0255751 A1 | 9/2018 | Regev |
| 2018/0256922 A1 | 9/2018 | Mittelstein |
| 2018/0257042 A1 | 9/2018 | Hester |
| 2018/0257076 A1 | 9/2018 | Weitz |
| 2018/0258160 A1 | 9/2018 | Lai |
| 2018/0258955 A1 | 9/2018 | Levasseur |
| 2018/0258957 A1 | 9/2018 | Levasseur |
| 2018/0296954 A1 | 10/2018 | Trampler |
| 2018/0353614 A1 | 12/2018 | Peters |
| 2018/0361053 A1 | 12/2018 | Fiering et al. |
| 2018/0361383 A1 | 12/2018 | Kapur et al. |
| 2018/0361384 A1 | 12/2018 | Kapur et al. |
| 2018/0369816 A1 | 12/2018 | Ai |
| 2018/0371418 A1 | 12/2018 | Yang et al. |
| 2019/0000932 A1 | 1/2019 | Martini |
| 2019/0000933 A1 | 1/2019 | Martini |
| 2019/0000947 A1 | 1/2019 | Weinschenk et al. |
| 2019/0000959 A1 | 1/2019 | Ciaramella et al. |
| 2019/0000982 A1 | 1/2019 | Wang et al. |
| 2019/0002497 A1 | 1/2019 | Stickel et al. |
| 2019/0002504 A1 | 1/2019 | Weinschenk et al. |
| 2019/0002561 A1 | 1/2019 | Galetto |
| 2019/0002573 A1 | 1/2019 | Galetto |
| 2019/0002578 A1 | 1/2019 | Brayshaw et al. |
| 2019/0002589 A1 | 1/2019 | Bardroff et al. |
| 2019/0002890 A1 | 1/2019 | Martini et al. |
| 2019/0004052 A1 | 1/2019 | Herd et al. |
| 2019/0008943 A1 | 1/2019 | Poolman et al. |
| 2019/0008948 A1 | 1/2019 | Ciaramella et al. |
| 2019/0010190 A1 | 1/2019 | Weinschenk et al. |
| 2019/0010192 A1 | 1/2019 | Binder et al. |
| 2019/0010471 A1 | 1/2019 | Zhang et al. |
| 2019/0010495 A1 | 1/2019 | Boitano et al. |
| 2019/0010514 A1 | 1/2019 | Poirot et al. |
| 2019/0011407 A9 | 1/2019 | Lipkens et al. |
| 2019/0015501 A1 | 1/2019 | Ciaramella et al. |
| 2019/0016753 A1 | 1/2019 | Jang et al. |
| 2019/0016767 A1 | 1/2019 | Shah |
| 2019/0016781 A1 | 1/2019 | Bolen |
| 2019/0022019 A1 | 1/2019 | Martini |
| 2019/0023577 A1 | 1/2019 | Feng |
| 2019/0024114 A1 | 1/2019 | Bauer |
| 2019/0030073 A1 | 1/2019 | Kalayoglu |
| 2019/0030151 A1 | 1/2019 | Jones et al. |
| 2019/0030533 A1 | 1/2019 | Shachar et al. |
| 2019/0031780 A1 | 1/2019 | Eavarone et al. |
| 2019/0031999 A1 | 1/2019 | Suresh et al. |
| 2019/0032036 A1 | 1/2019 | Zhang |
| 2019/0032052 A1 | 1/2019 | Zhang |
| 2019/0036152 A1 | 1/2019 | Gaben et al. |
| 2019/0036172 A1 | 1/2019 | Gaben et al. |
| 2019/0006036 A1 | 2/2019 | Moriarty et al. |
| 2019/0038671 A1 | 2/2019 | Fan et al. |
| 2019/0039060 A1 | 2/2019 | Chien et al. |
| 2019/0040099 A1 | 2/2019 | Brellisford et al. |
| 2019/0040117 A1 | 2/2019 | Elson et al. |
| 2019/0040414 A1 | 2/2019 | Wu |
| 2019/0046986 A1 | 2/2019 | Yuan et al. |
| 2019/0048060 A1 | 2/2019 | Conway et al. |
| 2019/0054112 A1 | 2/2019 | Gregoire |
| 2019/0054119 A1 | 2/2019 | Alma et al. |
| 2019/0054122 A1 | 2/2019 | Moriarity et al. |
| 2019/0055286 A1 | 2/2019 | Walz et al. |
| 2019/0055509 A1 | 2/2019 | Meacham et al. |
| 2019/0056302 A1 | 2/2019 | Berezin et al. |
| 2019/0056399 A1 | 2/2019 | Wong et al. |
| 2019/0060363 A1 | 2/2019 | Moriarity et al. |
| 2019/0062185 A1 | 2/2019 | Amouzadeh et al. |
| 2019/0062690 A1 | 2/2019 | Tostoes et al. |
| 2019/0062735 A1 | 2/2019 | Welstead et al. |
| 2019/0064146 A1 | 2/2019 | Glick |
| 2019/0067554 A1 | 2/2019 | Karrai et al. |
| 2019/0070233 A1 | 3/2019 | Yeung |
| 2019/0070528 A1 | 3/2019 | Luthe |
| 2019/0071695 A1 | 3/2019 | Wagner |
| 2019/0071717 A1 | 3/2019 | Zhang et al. |
| 2019/0076473 A1 | 3/2019 | Nguyen |
| 2019/0076769 A1 | 3/2019 | Meacham et al. |
| 2019/0078133 A1 | 3/2019 | Cavanagh et al. |
| 2019/0079070 A1 | 3/2019 | Shiffman et al. |
| 2019/0083533 A1 | 3/2019 | Soon-Shiong et al. |
| 2019/0085067 A1 | 3/2019 | Schurpf et al. |
| 2019/0085082 A1 | 3/2019 | Bicknell |
| 2019/0085381 A1 | 3/2019 | Neely et al. |
| 2019/0090900 A1 | 3/2019 | Rhee et al. |
| 2019/0091683 A1 | 3/2019 | Baudoin et al. |
| 2019/0092794 A1 | 3/2019 | Rubio Martinez et al. |
| 2019/0092865 A1 | 3/2019 | Ruiz-Opazo |
| 2019/0093097 A1 | 3/2019 | Madison et al. |
| 2019/0094185 A1 | 3/2019 | Athanassiadis |
| 2019/0101541 A1 | 4/2019 | Wandall et al. |
| 2019/0105043 A1 | 4/2019 | Jaworek et al. |
| 2019/0106039 A1 | 4/2019 | Winton et al. |
| 2019/0106710 A1 | 4/2019 | Zhang et al. |
| 2019/0107420 A1 | 4/2019 | Kincel |
| 2019/0111480 A1 | 4/2019 | Barbati et al. |
| 2019/0119387 A1 | 4/2019 | Brett |
| 2019/0119701 A1 | 4/2019 | Liang et al. |
| 2019/0125839 A1 | 5/2019 | Frederick et al. |
| 2019/0127685 A1 | 5/2019 | Fattah et al. |
| 2019/0133633 A1 | 5/2019 | Neurohr et al. |
| 2019/0135942 A1 | 5/2019 | Duthe et al. |
| 2019/0136261 A1 | 5/2019 | Conway |
| 2019/0143013 A1 | 5/2019 | Vincent et al. |
| 2019/0153027 A1 | 5/2019 | Natarajan et al. |
| 2019/0153106 A1 | 5/2019 | Ruiz-Opazo et al. |
| 2019/0160463 A1 | 5/2019 | Ai et al. |
| 2019/0161540 A1 | 5/2019 | Gearing et al. |
| 2019/0167722 A1 | 6/2019 | Soon-Shiong et al. |
| 2019/0169233 A1 | 6/2019 | Weinschenk et al. |
| 2019/0169597 A1 | 6/2019 | Astrakhan et al. |
| 2019/0169639 A1 | 6/2019 | Zhang et al. |
| 2019/0170745 A1 | 6/2019 | Hu et al. |
| 2019/0173129 A1 | 6/2019 | Gaben et al. |
| 2019/0175517 A1 | 6/2019 | Martini et al. |
| 2019/0175651 A1 | 6/2019 | Lee et al. |
| 2019/0176150 A1 | 6/2019 | Kapur et al. |
| 2019/0177368 A1 | 6/2019 | Weinschenk et al. |
| 2019/0177369 A1 | 6/2019 | Weinschenk et al. |
| 2019/0183931 A1 | 6/2019 | Alice et al. |
| 2019/0184035 A1 | 6/2019 | Jarjour et al. |
| 2019/0184312 A1 | 6/2019 | Liu et al. |
| 2019/0184326 A1 | 6/2019 | Davis et al. |
| 2019/0185860 A1 | 6/2019 | Kim et al. |
| 2019/0191252 A1 | 6/2019 | Lipkens et al. |
| 2019/0192653 A1 | 6/2019 | Hoge |
| 2019/0194049 A1 | 6/2019 | Lindemann |

(56) References Cited

U.S. PATENT DOCUMENTS

| | | |
|---|---|---|
| 2019/0194087 A1 | 6/2019 | Larsen |
| 2019/0194340 A1 | 6/2019 | Emtage et al. |
| 2019/0194617 A1 | 6/2019 | Emtage et al. |
| 2019/0199312 A1 | 6/2019 | Dasgupta et al. |
| 2019/0199322 A1 | 6/2019 | Dasgupta et al. |
| 2019/0201041 A1 | 7/2019 | Kimball et al. |
| 2019/0201047 A1 | 7/2019 | Yates et al. |
| 2019/0201048 A1 | 7/2019 | Nguyen et al. |
| 2019/0209616 A1 | 7/2019 | Galetto et al. |
| 2019/0211109 A1 | 7/2019 | Peshwa et al. |
| 2019/0218254 A1 | 7/2019 | Weinschenk et al. |
| 2019/0218602 A1 | 7/2019 | Zhang et al. |
| 2019/0218795 A1 | 7/2019 | Blomgren et al. |
| 2019/0225694 A1 | 7/2019 | Zien et al. |
| 2019/0225990 A1 | 7/2019 | Adbudl-Manan et al. |
| 2019/0290201 A1 | 7/2019 | Boudreaux et al. |
| 2019/0234964 A1 | 8/2019 | Wang |
| 2019/0240471 A1 | 8/2019 | Li et al. |
| 2019/0240976 A1 | 8/2019 | Foresti et al. |
| 2019/0241608 A1 | 8/2019 | Maloisel et al. |
| 2019/0241910 A1 | 8/2019 | Jarjour et al. |
| 2019/0246912 A1 | 8/2019 | Bahmanyar et al. |
| 2019/0247440 A1 | 8/2019 | Mata-Fink et al. |
| 2019/0248864 A1 | 8/2019 | Ellsworth et al. |
| 2019/0249157 A1 | 8/2019 | Friedland et al. |
| 2019/0256900 A1 | 8/2019 | Zhang et al. |

FOREIGN PATENT DOCUMENTS

| | | |
|---|---|---|
| CN | 1346056 A | 4/2002 |
| CN | 105 087 788 A | 11/2015 |
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| EP | 2675901 | 5/2018 |
| EP | 2956772 | 5/2018 |
| EP | 3323444 | 5/2018 |
| EP | 3324996 | 5/2018 |
| EP | 3327127 | 5/2018 |
| EP | 3337819 | 6/2018 |
| EP | 2772196 | 8/2018 |
| EP | 2882091 | 8/2018 |
| EP | 2910568 | 8/2018 |
| EP | 3265805 | 8/2018 |
| EP | 3359676 | 8/2018 |
| EP | 3360955 | 8/2018 |
| EP | 3361252 | 8/2018 |
| EP | 3362102 | 8/2018 |
| EP | 3363456 | 8/2018 |
| EP | 3363813 | 8/2018 |
| EP | 3365062 | 8/2018 |
| EP | 3365095 | 8/2018 |
| EP | 3365441 | 8/2018 |
| EP | 3365447 | 8/2018 |
| EP | 3366696 | 8/2018 |
| EP | 3367118 | 8/2018 |
| EP | 2931892 | 9/2018 |
| EP | 3019606 | 9/2018 |
| EP | 3089800 | 9/2018 |
| EP | 3123534 | 9/2018 |
| EP | 3368528 | 9/2018 |
| EP | 3368670 | 9/2018 |
| EP | 3371295 | 9/2018 |
| EP | 3372813 | 9/2018 |
| EP | 3372814 | 9/2018 |
| EP | 2535355 | 1/2019 |
| EP | 2922902 | 1/2019 |
| EP | 3004338 | 1/2019 |
| EP | 3421975 | 1/2019 |
| EP | 3423092 | 1/2019 |
| EP | 3423580 | 1/2019 |
| EP | 3425386 | 1/2019 |
| EP | 3426271 | 1/2019 |
| EP | 3426372 | 1/2019 |
| EP | 3426375 | 1/2019 |
| EP | 3426690 | 1/2019 |
| EP | 3427815 | 1/2019 |
| EP | 3429753 | 1/2019 |
| EP | 3430050 | 1/2019 |
| EP | 3430134 | 1/2019 |
| EP | 3430146 | 1/2019 |
| EP | 3430463 | 1/2019 |
| EP | 3433363 | 1/2019 |
| EP | 3433366 | 1/2019 |
| EP | 3434774 | 1/2019 |
| EP | 3434776 | 1/2019 |
| EP | 2598533 | 2/2019 |
| EP | 2691422 | 2/2019 |
| EP | 2925431 | 2/2019 |
| EP | 3170185 | 2/2019 |
| EP | 3436030 | 2/2019 |
| EP | 3436196 | 2/2019 |
| EP | 3436575 | 2/2019 |
| EP | 3436579 | 2/2019 |
| EP | 3437740 | 2/2019 |
| EP | 3439698 | 2/2019 |
| EP | 3440191 | 2/2019 |
| EP | 3441468 | 2/2019 |
| EP | 3442598 | 2/2019 |
| EP | 3443002 | 2/2019 |
| EP | 3443084 | 2/2019 |
| EP | 3445407 | 2/2019 |

(56) References Cited

FOREIGN PATENT DOCUMENTS

| | | |
|---|---|---|
| EP | 3445848 | 2/2019 |
| EP | 3445853 | 2/2019 |
| EP | 3445856 | 2/2019 |
| EP | 2694091 | 3/2019 |
| EP | 3080260 | 3/2019 |
| EP | 3448291 | 3/2019 |
| EP | 3448995 | 3/2019 |
| EP | 3449850 | 3/2019 |
| EP | 3452133 | 3/2019 |
| EP | 3452499 | 3/2019 |
| EP | 3453406 | 3/2019 |
| EP | 3456339 | 3/2019 |
| EP | 3458081 | 3/2019 |
| EP | 3458083 | 3/2019 |
| EP | 3458104 | 3/2019 |
| EP | 3458105 | 3/2019 |
| EP | 3458107 | 3/2019 |
| EP | 3458108 | 3/2019 |
| EP | 3458590 | 3/2019 |
| EP | 3066115 | 4/2019 |
| EP | 3119807 | 4/2019 |
| EP | 3186281 | 4/2019 |
| EP | 3361252 | 4/2019 |
| EP | 3463433 | 4/2019 |
| EP | 3463660 | 4/2019 |
| EP | 3464198 | 4/2019 |
| EP | 3464594 | 4/2019 |
| EP | 3467276 | 4/2019 |
| EP | 3467491 | 4/2019 |
| EP | 3468225 | 4/2019 |
| EP | 3468351 | 4/2019 |
| EP | 3468594 | 4/2019 |
| EP | 3470089 | 4/2019 |
| EP | 3470519 | 4/2019 |
| EP | 3471621 | 4/2019 |
| EP | 3473707 | 4/2019 |
| EP | 2546144 | 5/2019 |
| EP | 3311588 | 5/2019 |
| EP | 3474904 | 5/2019 |
| EP | 3475307 | 5/2019 |
| EP | 3481361 | 5/2019 |
| EP | 3481867 | 5/2019 |
| EP | 2412817 | 6/2019 |
| EP | 3490562 | 6/2019 |
| EP | 3490574 | 6/2019 |
| EP | 3490694 | 6/2019 |
| EP | 3490712 | 6/2019 |
| EP | 3490801 | 6/2019 |
| EP | 3491124 | 6/2019 |
| EP | 3491126 | 6/2019 |
| EP | 3493836 | 6/2019 |
| EP | 3493907 | 6/2019 |
| EP | 3495376 | 6/2019 |
| EP | 3495811 | 6/2019 |
| EP | 3498846 | 6/2019 |
| EP | 3500244 | 6/2019 |
| EP | 3500271 | 6/2019 |
| EP | 3500297 | 6/2019 |
| EP | 3500659 | 6/2019 |
| EP | 3500696 | 6/2019 |
| EP | 3501619 | 6/2019 |
| EP | 3502137 | 6/2019 |
| EP | 3502253 | 6/2019 |
| EP | 510161 | 7/2019 |
| EP | 2680877 | 7/2019 |
| EP | 2996789 | 7/2019 |
| EP | 3068535 | 7/2019 |
| EP | 3140319 | 7/2019 |
| EP | 3277333 | 7/2019 |
| EP | 3505098 | 7/2019 |
| EP | 3511342 | 7/2019 |
| EP | 3511420 | 7/2019 |
| EP | 3512540 | 7/2019 |
| EP | 2643015 | 8/2019 |
| EP | 2723380 | 8/2019 |
| EP | 3043761 | 8/2019 |
| EP | 3207130 | 8/2019 |
| EP | 3524193 | 8/2019 |
| EP | 3526326 | 8/2019 |
| EP | 3526334 | 8/2019 |
| EP | 3527282 | 8/2019 |
| GB | 2 420 510 A | 5/2006 |
| JP | 2-290266 | 11/1990 |
| JP | 9-136090 | 5/1997 |
| JP | H11-090110 | 4/1999 |
| JP | 2005-249267 | 12/2005 |
| KR | 10-2004-0053133 A | 6/2004 |
| KR | 1442486 | 9/2014 |
| RU | 2037327 C1 | 6/1995 |
| RU | 94015846 | 6/1996 |
| RU | 2067079 | 9/1996 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/130321 | 10/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043046 | 3/2013 |
| WO | WO 2013/043297 A1 | 3/2013 |
| WO | WO 2013030691 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | 2013/187382 A1 | 12/2013 |
| WO | WO 2014/014941 A1 | 1/2014 |
| WO | WO 2014/029505 | 2/2014 |
| WO | WO 2014/035457 | 3/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2014/165177 | 10/2014 |
| WO | WO 2015/006730 | 1/2015 |
| WO | 2015/102528 A1 | 7/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/011519 | 1/2017 |
| WO | WO 2017/021543 | 2/2017 |
| WO | WO 2017/041102 | 3/2017 |
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |

(56) References Cited

FOREIGN PATENT DOCUMENTS

| | | |
|---|---|---|
| WO | WO 2018011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018058275 | 5/2018 |
| WO | WO 2018081476 | 5/2018 |
| WO | WO 2018091879 | 5/2018 |
| WO | WO2018094244 | 5/2018 |
| WO | WO 20180814701 | 5/2018 |
| WO | WO 2018098671 | 6/2018 |
| WO | WO 2018102752 | 6/2018 |
| WO | WO 2018106163 | 6/2018 |
| WO | WO 2018112145 | 6/2018 |
| WO | WO 2018112335 | 6/2018 |
| WO | WO 2018138385 | 8/2018 |
| WO | WO 2018140573 | 8/2018 |
| WO | WO 2018140845 | 8/2018 |
| WO | WO 2018142364 | 8/2018 |
| WO | WO 2018151811 | 8/2018 |
| WO | WO 2018151823 | 8/2018 |
| WO | WO 2018153772 | 8/2018 |
| WO | WO 2018160548 | 9/2018 |
| WO | WO 2018160909 | 9/2018 |
| WO | WO 2018160993 | 9/2018 |
| WO | WO 2018161017 | 9/2018 |
| WO | WO 2018161026 | 9/2018 |
| WO | WO 2018161038 | 9/2018 |
| WO | WO 2018161905 | 9/2018 |
| WO | WO 2018163183 | 9/2018 |
| WO | WO2018227286 | 12/2018 |
| WO | WO2018229612 | 12/2018 |
| WO | WO2018231990 | 12/2018 |
| WO | WO2018232045 | 12/2018 |
| WO | WO2018232131 | 12/2018 |
| WO | WO2018234421 | 12/2018 |
| WO | WO2018235228 | 12/2018 |
| WO | WO2018236708 | 12/2018 |
| WO | WO2018237201 | 12/2018 |
| WO | WO2018237239 | 12/2018 |
| WO | WO2018183966 | 1/2019 |
| WO | WO2019002551 | 1/2019 |
| WO | WO2019002633 | 1/2019 |
| WO | WO2019005155 | 1/2019 |
| WO | WO2019005866 | 1/2019 |
| WO | WO2019005871 | 1/2019 |
| WO | WO2019006418 | 1/2019 |
| WO | WO2019007869 | 1/2019 |
| WO | WO2019008335 | 1/2019 |
| WO | WO2019010422 | 1/2019 |
| WO | WO2019018423 | 1/2019 |
| WO | WO2019018491 | 1/2019 |
| WO | WO2019018796 | 1/2019 |
| WO | WO2019022671 | 1/2019 |
| WO | WO2019023523 | 1/2019 |
| WO | WO2019025661 | 2/2019 |
| WO | WO2019025984 | 2/2019 |
| WO | WO2019028172 | 2/2019 |
| WO | WO2019032675 | 2/2019 |
| WO | WO2019036382 | 2/2019 |
| WO | WO209048639 | 3/2019 |
| WO | WO2019041344 | 3/2019 |
| WO | WO2019046450 | 3/2019 |
| WO | WO2019048666 | 3/2019 |
| WO | WO2019051106 | 3/2019 |
| WO | WO2019051255 | 3/2019 |
| WO | WO2019051278 | 3/2019 |
| WO | WO2019051316 | 3/2019 |
| WO | WO2019051355 | 3/2019 |
| WO | WO2019055697 | 3/2019 |
| WO | WO2019055817 | 3/2019 |
| WO | WO2019055896 | 3/2019 |
| WO | WO2019056015 | 3/2019 |
| WO | WO2019057774 | 3/2019 |
| WO | WO2019058321 | 3/2019 |
| WO | WO2019058326 | 3/2019 |
| WO | WO2019060253 | 3/2019 |
| WO | WO2019060425 | 3/2019 |
| WO | WO2019060779 | 3/2019 |
| WO | WO2019067015 | 4/2019 |
| WO | WO2019069101 | 4/2019 |
| WO | WO2019070541 | 4/2019 |
| WO | WO2019070974 | 4/2019 |
| WO | WO2019072889 | 4/2019 |
| WO | WO2019075409 | 4/2019 |
| WO | WO2019079497 | 4/2019 |
| WO | WO2019079819 | 4/2019 |
| WO | WO2019080898 | 5/2019 |
| WO | WO2019081521 | 5/2019 |
| WO | WO2019094360 | 5/2019 |
| WO | WO2019098839 | 5/2019 |
| WO | WO2019099619 | 5/2019 |
| WO | WO2019099736 | 5/2019 |
| WO | WO2019099949 | 5/2019 |
| WO | WO2019101691 | 5/2019 |
| WO | WO2019101956 | 5/2019 |
| WO | WO201912655 | 6/2019 |
| WO | WO2018215686 | 6/2019 |
| WO | WO2019111250 | 6/2019 |
| WO | WO2019113310 | 6/2019 |
| WO | WO2019118475 | 6/2019 |
| WO | WO2019118885 | 6/2019 |
| WO | WO2019126329 | 6/2019 |
| WO | WO2019126558 | 6/2019 |
| WO | WO2019126724 | 6/2019 |
| WO | 2019139650 | 7/2019 |
| WO | WO2019134007 | 7/2019 |
| WO | WO2019135843 | 7/2019 |
| WO | WO2019136288 | 7/2019 |
| WO | WO2019140019 | 7/2019 |
| WO | WO2019139650 | 8/2019 |
| WO | WO2019144659 | 8/2019 |
| WO | WO 2018231759 | 12/2019 |

OTHER PUBLICATIONS

Alvarez et al.; Shock Waves, vol. 17, No. 6, pp. 441-447, 2008.

Augustsson et al., Acoustophoretic microfluidic chip for sequential elution of surface bound molecules from beads or cells, Biomicrofluidics, Sep. 2012, 6(3):34115.

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

(56) References Cited

OTHER PUBLICATIONS

Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Ding, X et al., "Cell Separation Using Tilted-Angle Standing Surface Acoustic Waves", Proceedings of the National Academy of Sciences, Sep. 9, 2014, vol. 111, No. 36, pp. 12992-12997, See abstract; p. 12994, left column p. 12995, left column; figure 1-3 and 6.
Ensminger et al.; Ultrasonics Fundamentals, Technologies, and Applications; 2011.
Evander et al; Acoustofluidics 20: Applications in acoustic trapping, Lab Chip, 2012, 12,4667-4676.
Evander et al.; Acoustiofluidics 5: Building microfluidic acoustic resonators, Lab Chip, 2012, 12, 684.
Gallego-Juarez et al; "Piezoelectric ceramic and ultrasonic transducers"; Journal of Physics E: Scientific Instruments. 1989.
Ganguly et al; Essential Physics for Radiology and Imaging; Academic Publishers, Jan. 2016.
Garcia-Lopez, et al; Enhanced Acoustic Separation of Oil-Water Emulsion in Resonant Cavities. The Open Acoustics Journal. 2008, vol. 1, pp. 66-71.
Greenhall et al; Dynamic behavior of microscale particles controlled by standing bulk acoustic waves; Applied Physics Letters, 105, 144105 (2014).
Grenvall et al.; Concurrent Isolation of Lymphocytes and Granulocytes Using Prefocused Free Flow Acoustophoresis; Analytical Chemistry; vol. 87; pp. 5596-5604; 2015.
Gorenflo et al.; Characterization and Optimization of Acoustic Filter Performance by Experimental DesignMethodology (whole document).
Gor'Koy et al.; On the Forces Acting on a Small Particle in an Acoustical Field in an Ideal Fluid; Soviet Physics Doklady, vol. 6, p. 773.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Jin et al; Pharmaceutical Engineering; Jan. 2015; vol. 35 No. 1.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
National Science Foundation, "Catalyzing Commercialization: putting sound to work for challenging separations", CEP, Sep. 2015, p. 14.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Nienow et al.; A potentially scalable method for the harvesting of hMSCs from microcarriers; Biochemical Engineering Journal 85 (2014) 79-88.
Pangu et al.; Droplet transport and coalescence kinetics in emulsions subjected to acoustic fields; Ultrasonics 46, pp. 289-302 (2007).
Phys.org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNAN0.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al., J. Chem. Edu., 1990, 67(9), p. 763, published Sep. 1990.
Shitizu et al; "A Tutorial Review on Bioprocessing Systems Engineering" (whole document).
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-1196; 2012.
Woodside et al.; Acoustic Force Distribution in Resonators for Ultrasonic Particle Separation; Biotechnology Laboratory and Dept of Chemical and Bio-Resource Engineering, University of British Columbia, Sep. 1998, vol. 44, No. 9.
Zhanqiu et al ;Culture Conditions and Types of Growth Media for Mammalian Cells (whole document).
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.

(56) References Cited

OTHER PUBLICATIONS

International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 Dated Jun. 21, 2013.
International Search Report and Written Opinion for International Application No. PCT/US2013/032705 dated Jul. 26, 2013.
International Search Report and Written Opinion for International Application No. PCT/US2013/050729 Dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
European Search Report of European Application No. 12825592.4 dated Apr. 28, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
International Search Report and Written Opinion for International Application No. PCT/US2018/026617, dated Jul. 4, 2018.
International Search Report and Written Opinion for International Application No. PCT/US2018/31267, dated Aug. 1, 2018.
European Search Report of European Application No. 15847217.5 dated Oct. 15, 2018.
International Search Report and Written Opinion for International Application No. PCT/US2017/057485, dated Apr. 23, 2019.
/International Search Report and Written Opinion for International Application No. PCT/US18/65839, dated May 16, 2019.
International Search Report and Written Opinion for International Application No. PCT/US19/12950, dated May 24, 2019.
International Search Report and Written Opinion for International Application No. PCT/US18/63698, dated May 27, 2019.
International Search Report and Written Opinion for International Application No. PCT/US19/21492, dated Jun. 25, 2019.
Notice of Allowability received for U.S. Appl. No. 15/788,784, dated Apr. 29, 2022, 2 Pages.
Notice of Allowance received for U.S. Appl. No. 15/788,784, dated Apr. 13, 2022, 9 Pages.
Office Action received for Chinese Patent Application No. 201780070614.9 dated May 31, 2022, 15 pages (7 Pages of English Translation & 8 Pages of Official Copy).
Loos et al., "Functionalized polystyrene nanoparticles as a platform for studying bio-nano interactions", Beilstein Journal Nanotechnology, Issue 5 No. 1, 2014, pp. 2403-2412.
Office Action received for Korean Patent Application No. 10-2019-7014501, dated Nov. 23, 2022, 7 Pages (3 Pages of English Translation & 4 Pages of Official copy).
Office Action received for Japanese Patent Application No. 2019-543176 dated Apr. 4, 2022, 13 Pages (6 Pages of English Translation and 7 Pages of Official Copy).
Office Action received for Chinese Patent Application No. 201780070614.9 dated Feb. 1, 2023, 17 Pages (9 Pages of English Translation & 8 Pages of Official Copy).
Notice of Final Rejection issued in Korean Patent Application No. 10-2019-7014501, dated Apr. 20, 2023, 7 pages (4 pages of Official Copy & 3 pages of English Translation).

\* cited by examiner

ACOUSTIC CELL SEPARATION TECHNIQUES AND PROCESSES

CROSS-REFERENCE TO RELATED APPLICATIONS

This application claims the benefit of U.S. Provisional Patent Application Ser. No. 62/675,194, filed on May 23, 2018, and claims the benefit of U.S. Provisional Patent Application Ser. No. 62/679,012, filed on May 31, 2018, and is a continuation-in-part of U.S. patent application Ser. No. 16/010,296, filed on Jun. 15, 2018, which claims the benefit of U.S. Provisional Patent Application Ser. No. 62/520,488, filed on Jun. 15, 2017, and which is a continuation-in-part of U.S. patent application Ser. No. 15/916,270, filed on Mar. 8, 2018, which claims the benefit of U.S. Provisional Patent Application Ser. No. 62/468,895, filed on Mar. 8, 2017. This application is also a continuation-in-part of U.S. patent application Ser. No. 15/586,116, filed on May 3, 2017, which claims the benefit of U.S. Provisional Patent Application Ser. No. 62/330,947, filed on May 3, 2016, and U.S. Provisional Patent Application Ser. No. 62/359,182, filed on Jul. 6, 2016, and U.S. Provisional Patent Application Ser. No. 62/374,910, filed on Aug. 15, 2016. This application is also a continuation-in-part of U.S. patent application Ser. No. 15/788,784, filed on Oct. 19, 2017, which claims the benefit of U.S. Provisional Patent Application Ser. No. 62/410,312, filed on Oct. 19, 2016. This application is a continuation-in-part of U.S. patent application Ser. No. 15/942,316, filed on Mar. 30, 2018, which claims the benefit of U.S. Provisional Patent Application Ser. No. 62/479,309, filed on Mar. 30, 2017; and U.S. Provisional Patent Application Ser. No. 62/485,229, filed on Apr. 13, 2017, and is a continuation-in-part of U.S. patent application Ser. No. 15/613,790, filed on Jun. 5, 2017, which is a divisional of U.S. patent application Ser. No. 15/143,481, filed on Apr. 29, 2016, now U.S. Pat. No. 9,670,477, issued on Jun. 6, 2017, which claims the benefit of U.S. Provisional Patent Application Ser. No. 62/316,933, filed on Apr. 1, 2016; and U.S. Provisional Patent Application Ser. No. 62/154,690, filed on Apr. 29, 2015. The entire disclosures of these applications are hereby fully incorporated herein by reference.

BACKGROUND

Separation of biomaterial has been applied in a variety of contexts. For example, separation techniques for separating proteins from other biomaterials are used in a number of analytical processes.

SUMMARY

Separation of biomaterials can be accomplished by functionalized material distributed in a fluid chamber that bind the specific target materials such as recombinant proteins and monoclonal antibodies or cells. The functionalized material, such as beads that are coated with an affinity protein, is trapped by nodes and/or anti-nodes of an acoustic standing wave. In this approach, the functionalized material is trapped without contact (without, for example, using mechanical channels, conduits, tweezers, etc.).

BRIEF DESCRIPTION OF THE DRAWINGS

The drawings are described in more detail below, with reference to the accompanying drawings, in which.

DETAILED DESCRIPTION

The affinity separation of biological materials, such as proteins or cells, is accomplished through the use of a ligand that is covalently bonded to a surface, such as a microbead, interacts with the protein or cell such that the protein or cell is bound to the ligand on the microbead.

A ligand is a substance that forms a complex with the biomolecules. With protein-ligand binding, the ligand is usually a molecule which produces a signal by binding to a site on a target protein the binding typically results in a change of confirmation of target protein. The ligand can be a small molecule, ion, or protein which binds to the protein material. The relationship between ligand and binding partner is a function of charge, hydrophobicity, and molecular structure. Binding occurs by intermolecular forces such as ionic bonds, hydrogen bonds and van der Waals forces. The Association of docking is actually reversible through disassociation. Measurably irreversible covalent bonds between the ligand and target molecule is typical in biological systems.

A ligand that can bind to a receptor, alter the function of the receptor, and trigger a physiological response is called an agonist for the receptor. Agonist binding to receptor can be characterized both in terms of how much physiological response can be triggered and in terms of the concentration of the agonist that is required to produce the physiological response. High affinity ligand binding implies that the relatively low concentration of the ligand is adequate to maximally occupy a ligand—binding site and trigger a physiological response. The lower the $K_i$ level is, the more likely there will be a chemical reaction between the pending and the receptive antigen. Low—affinity binding (high $K_i$ level) implies that a relatively high concentration of the ligand is required before the binding site is maximally occupy and the maximum physiological response to the ligand is achieved. Bivalent ligands consist of two connected molecules as ligands, and are used in scientific research to detect receptor timers and to investigate the properties.

The T cell receptor, or TCR, is a molecule found on the surface of T cells or T lymphocytes, that is responsible for recognizing fragments of antigen as peptides bound to major histocompatibility complex (MHC) molecules. The binding between TCR and antigen peptides is of relatively low affinity and is degenerative.

Figure 1:
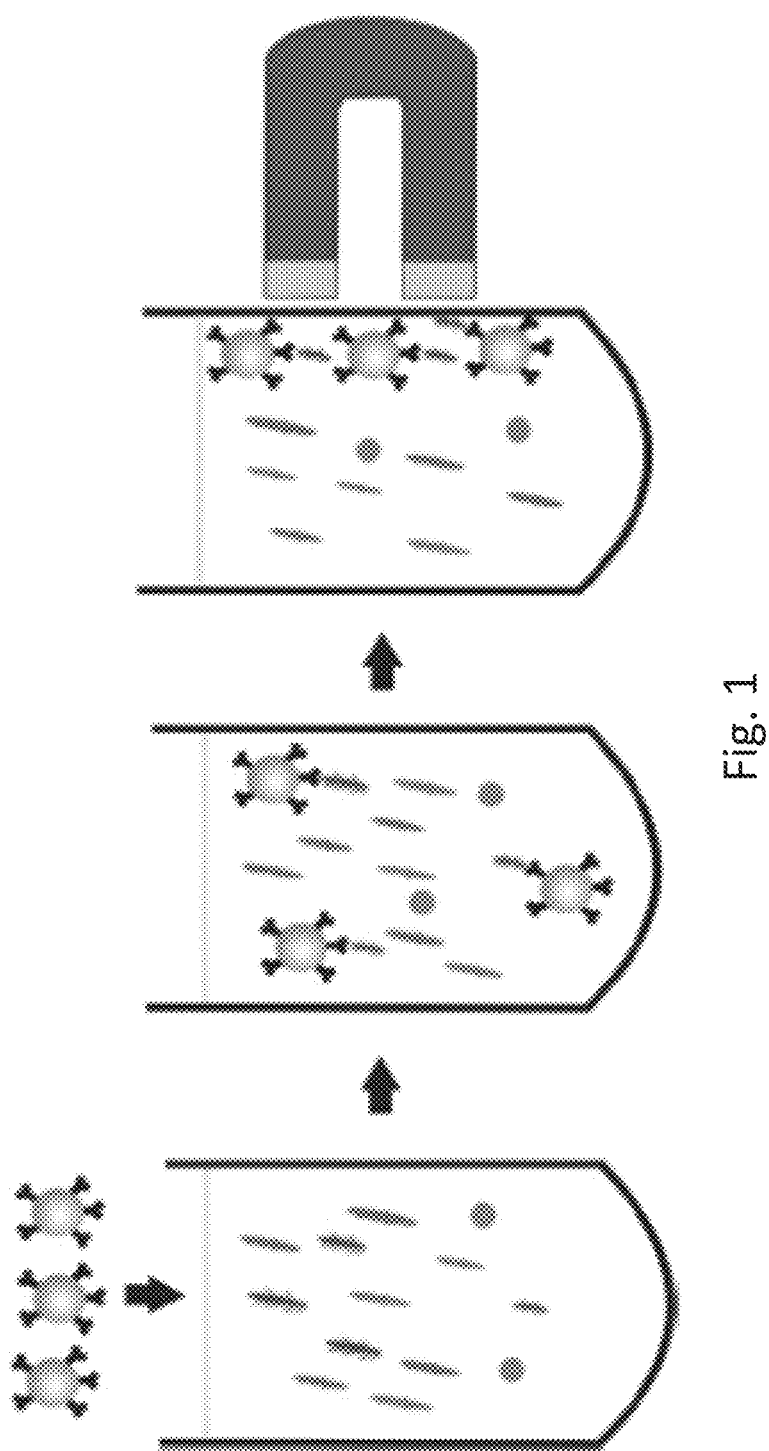
FIG. 1 is a diagram of a separation process using paramagnetic beads in a magnetic field.

Referring to FIG. 1, paramagnetic beads, such as iron or ferro-magnetic beads sold under the name Dynabeads, have been used to achieve affinity extraction. The magnetic beads, coated with a functionalized material, bind to biological targets in complex mixtures to permit the target material to be separated out of the complex mixture using a magnetic field. The beads carry molecules for affine binding various targets with high specificity. The beads are injected into the complex mixture and incubated to bind the targets. The beads are extracted by a magnet together with the targets attached to the beads.

Micro sized beads are available, such as, e.g., Dynabeads, which are on the order of 4.5 μm in size. Nano sized beads may be used, such as, e.g., Myltenyi, which are on the order of 50 nm in size. Some of the affine molecules that may be used include antibodies, aptamers, oligonucleotides and receptors, among others. The targets for the affinity binding may include biomolecules, cells, exosomes, drugs, etc.

Figure 2:
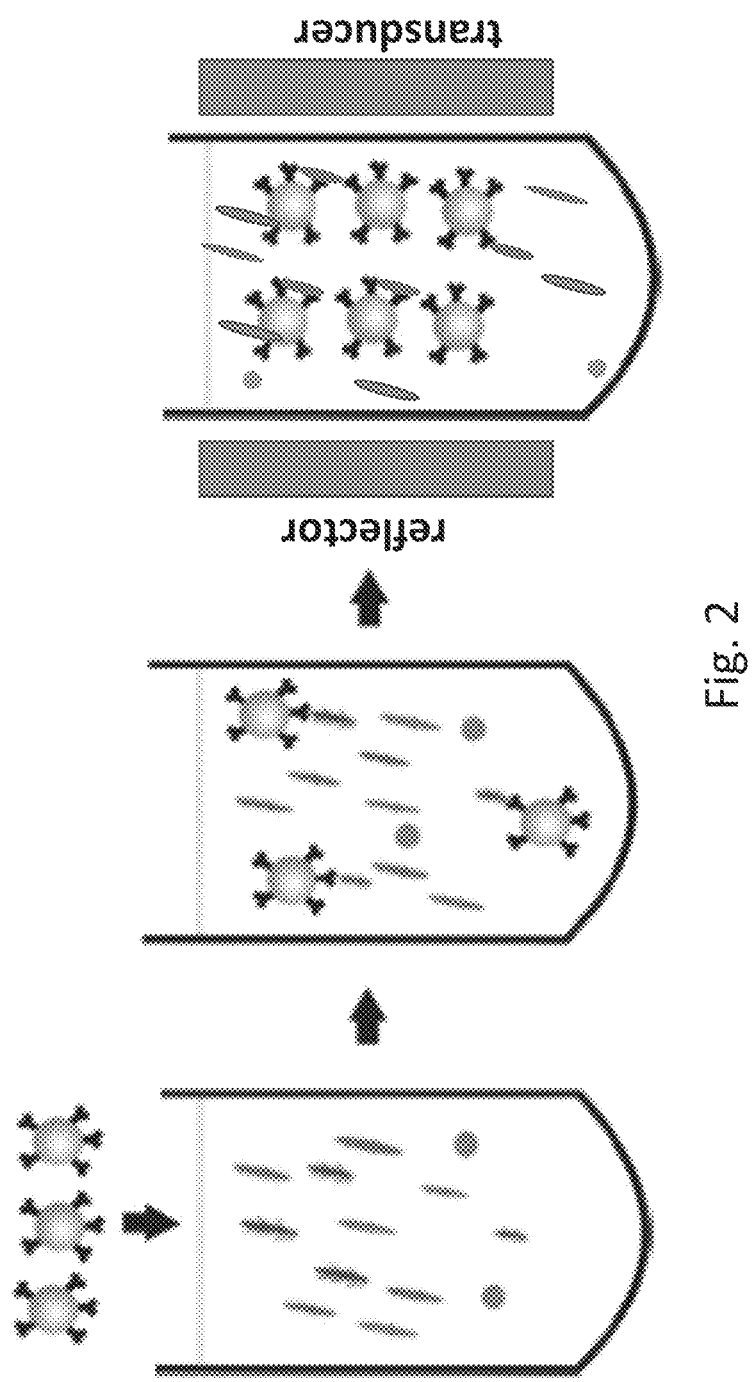
FIG. 2 is a diagram of a separation process using acoustic beads in an acoustic field.

Referring to FIG. 2, beads with high acoustic contrast and affinity chemistry are illustrated. These acoustic beads can be used in exactly the same way as magnetic beads with regard to having functionalized material coatings or composition for affinity binding. The acoustic beads are designed to be extracted from a complex mixture or fluid with an acoustic field. The acoustic beads can be directly used in all the applications developed in cell manufacturing, biochemistry, diagnostics, sensors, etc. that use magnetic beads.

The acoustic beads can use the same surface and affinity chemistry as is used with magnetic beads. This ease of substitution of acoustic beads for magnetic beads has many advantages, including simplifying approval for applications, as well as simplifying the applications.

The acoustic beads can be made biocompatible. Such beads can be produced in different sizes, which permits continuous separation based on size in a size differentiating acoustic field, such as may be provided with an angled-field fractionation technology. The acoustic beads can be combined with an enclosed acoustics-based system, leading to a continuous end-to-end cycle for therapeutic cell manufacturing. This functionality provides an alternative to magnetic bead extraction, while preserving use of currently existing affinity chemistry, which can be directly transferred to the acoustic beads. The acoustic beads may be a consumable product in the separation operation.

In an example, a proof of concept trial was made using the published Memorial Sloan Kettering Cancer Center (MSKCC) protocol for extraction of CD3+ T cells from patient's blood. In the trial, paramagnetic beads were used, and the magnetic field is replaced with an acoustic field. The process of extracting CD3+ T cells from patient's blood is an integral part of manufacturing CAR (chimeric antigen receptor) T cells. Current processes are based on commercially available CD3 Dynabeads. In the trial, efforts were made to minimize the protocol differences, including performing the experiments in culture broth, rather than blood. The difference is considered reduced since several steps in CAR T cell manufacturing work from broth. The solvent density was increased to make T cells "acoustically invisible," or not as susceptible to an acoustic field. The small size of the Dynabeads may provide an acoustic contrast that is similar to the cells, thus making separation tolerances smaller. The trial employed Jurkat CD3+ and CD3− T cell lines as models. The CD3− cells were employed as a control for non-specific trapping.

Figure 4:
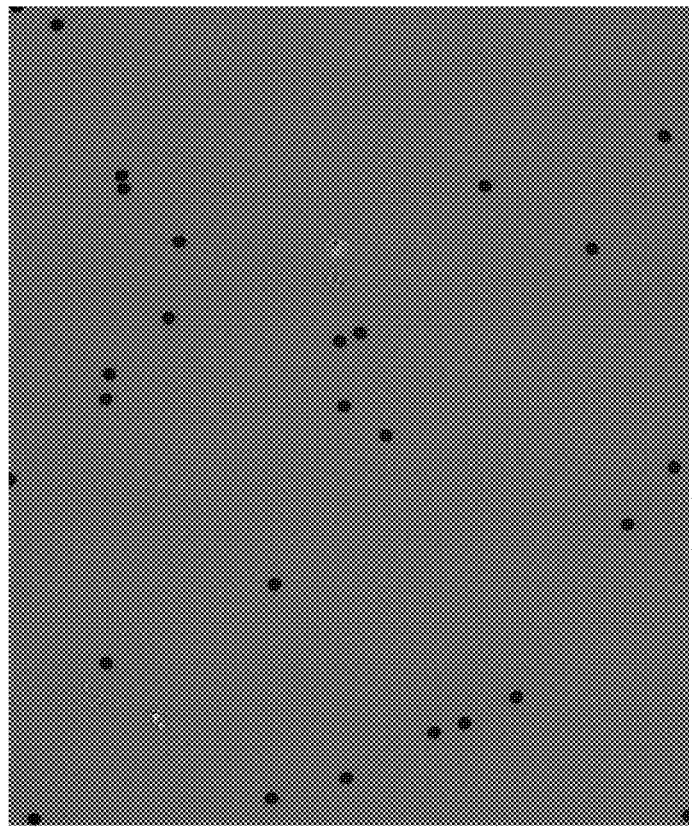
FIG. 4 is an image of beads without CD3− T-cells to demonstrate specificity of selection.
Figure 3:
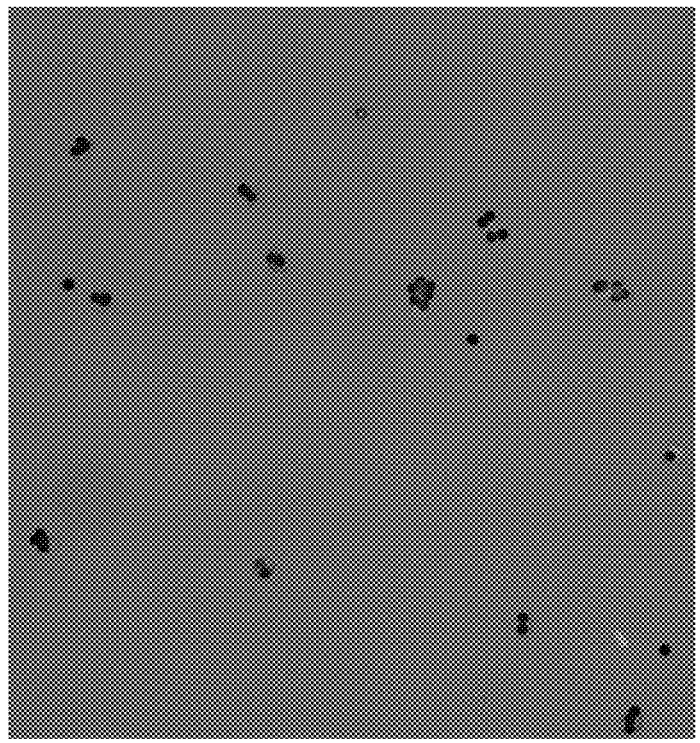
FIG. 3 is an image of CD3+ T-cell complexes with beads.

Referring now to FIGS. 3 and 4, images of results of the trial are shown. The cell suspensions were incubated with CD3 Dynabeads, which bound CD3+ cells. The mixture was passed through the acoustic system, which trapped the magnetic beads (with or without cells). The collected cells were successfully growing in culture. The images in FIGS. 3 and 4 are obtained with overlap of bright field images with fluorescence images. The beads are black with slight reddish autofluorescence. The live cells are fluorescent red. The bead diameter is 4.5 microns. FIG. 3 shows CD3+ T-cell complexes with beads, which demonstrates the efficiency of the technique. FIG. 4 shows that no CD3− T-cells have been extracted, which demonstrates the specificity and selectivity of the technique.

Figure 6:
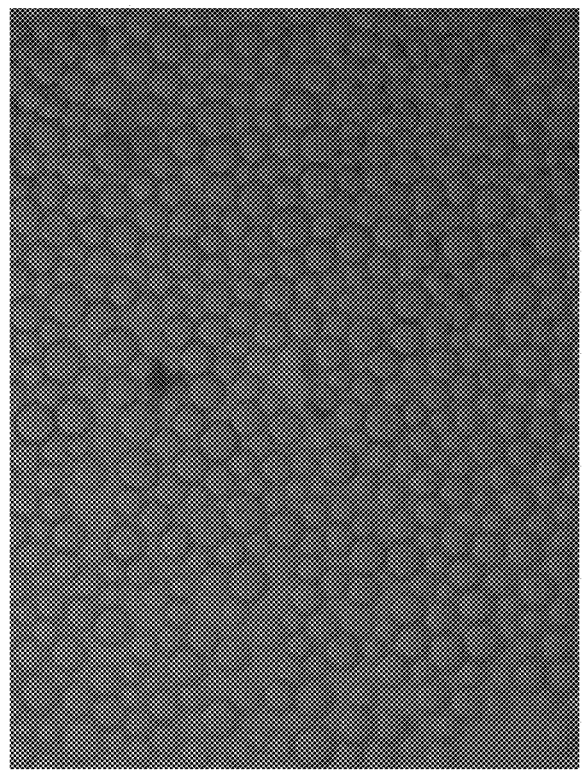
FIG. 6 is an image of homogenous agarose beads.
Figure 5:
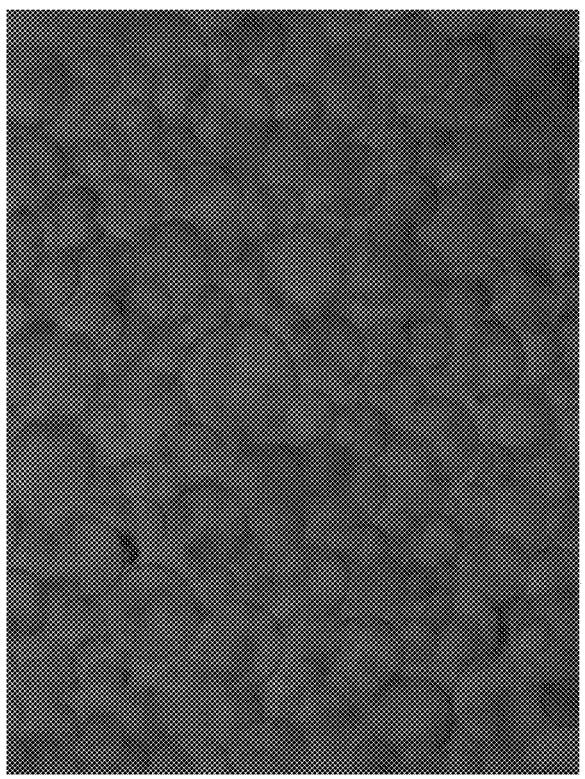
FIG. 5 is an image of heterogenous beads available with streptavidin and biotin conjugates.

Referring now to FIGS. 5 and 6, results of a trial with acoustic beads is shown. In this trial, agarose beads were used as the acoustic beads. These beads are available off-shelf from several manufacturers, and are not paramagnetic or have little to none iron or ferro magnetic content. Some agarose beads have surface modifications that simplify antibody attachment. They are also composed of biocompatible material, which can be important for therapeutic solutions. FIG. 5 shows ABTBeads, which are relatively inexpensive, heterogeneous (20-150 μm), off-shelf beads, which are available with streptavidin and biotin conjugates. FIG. 6 shows CellMosaic agarose beads, which tend to be relatively expensive, homogeneous (20-40 μm), and can be configured with any modification by order.

Figure 7:
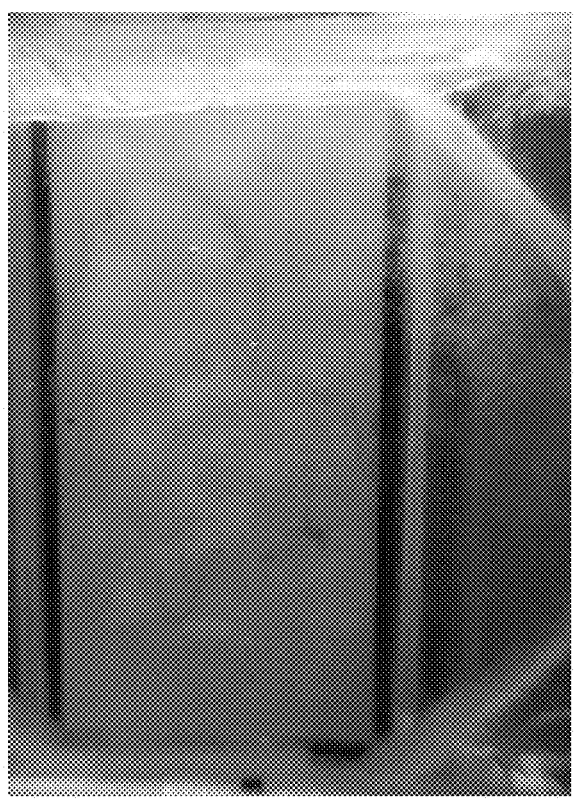
FIG. 7 is a photograph of a miniature acoustic system for processing beads.

The acoustic beads can be trapped in an acoustic field, such as a multi-dimensional acoustic standing wave. Referring to FIG. 7, a miniature acoustic system developed for acoustic applications is shown, which is used for trapping the acoustic beads. The smaller size of the system contributes to reducing the need for larger amounts of expensive reagents and permits processing of small volume samples.

Figure 8:
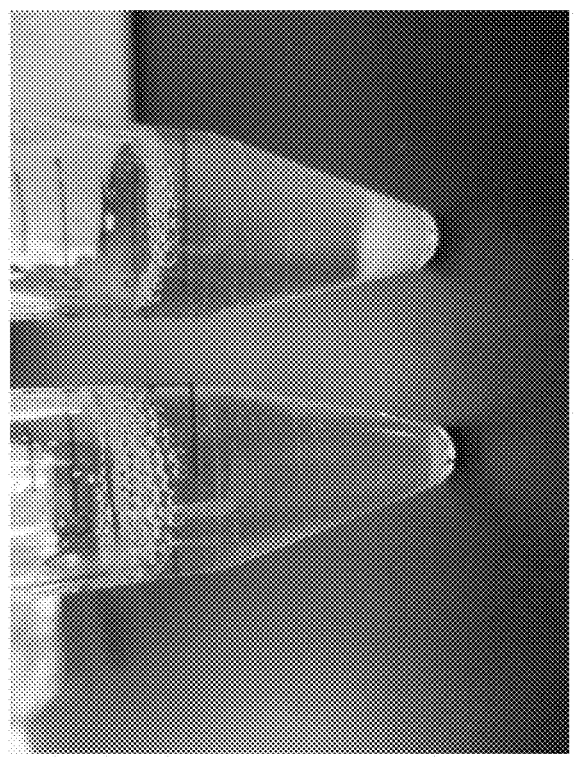
FIG. 8 is a photograph of a separation result.

Referring to FIG. 8, CellMosaic agarose beads escaped (left tube) and trapped (right) in the acoustic system are shown. The acoustic system trapping efficiency can be 90%+.

Figure 9:
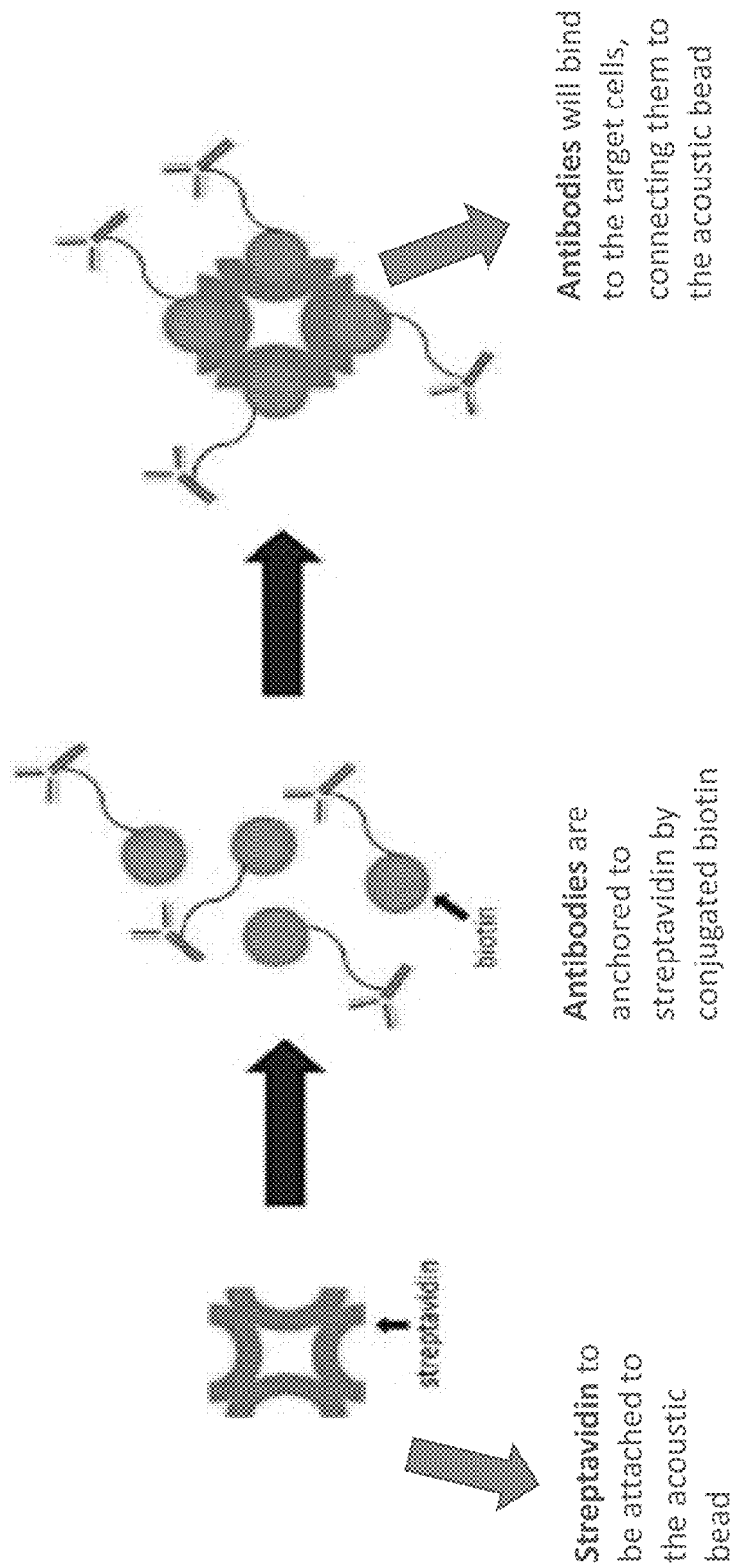
FIG. 9 is a diagram of an affinity technique that may be used with beads.

Referring to FIG. 9, a flexible approach to activating the acoustic beads is illustrated. In this approach, antibodies are attached to agarose beads using a streptavidin-biotin complex. The complex is widely used in biochemistry, and very stable. Agarose beads with conjugated streptavidin are available commercially as are antibody-biotin conjugates.

Figure 10:
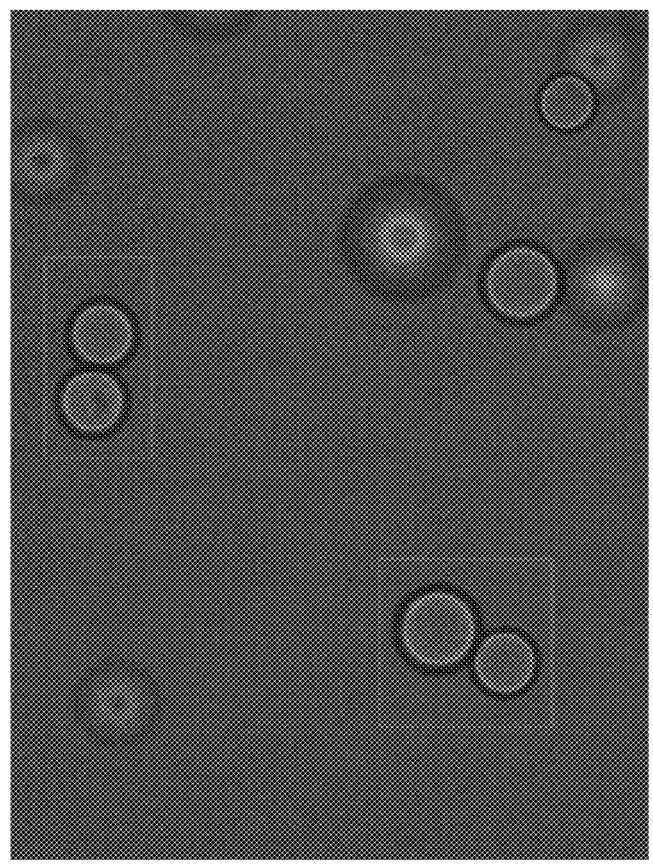
FIGS. 10, 11 and 12 are microphotographs of streptevidin-conjugated and biotin-conjugated beads that form complexes with each other.
Figure 12:
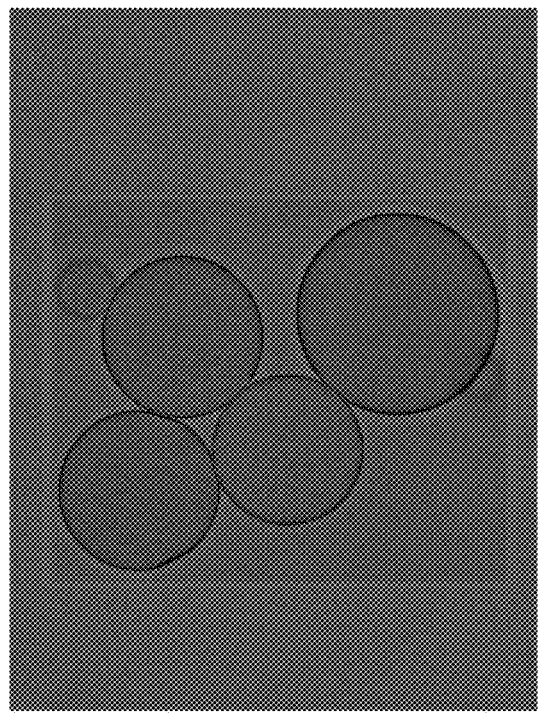
Figure 11:
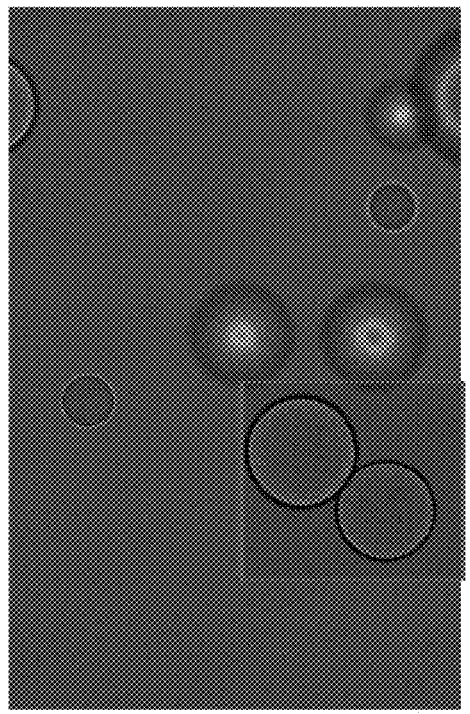
Figure 13:
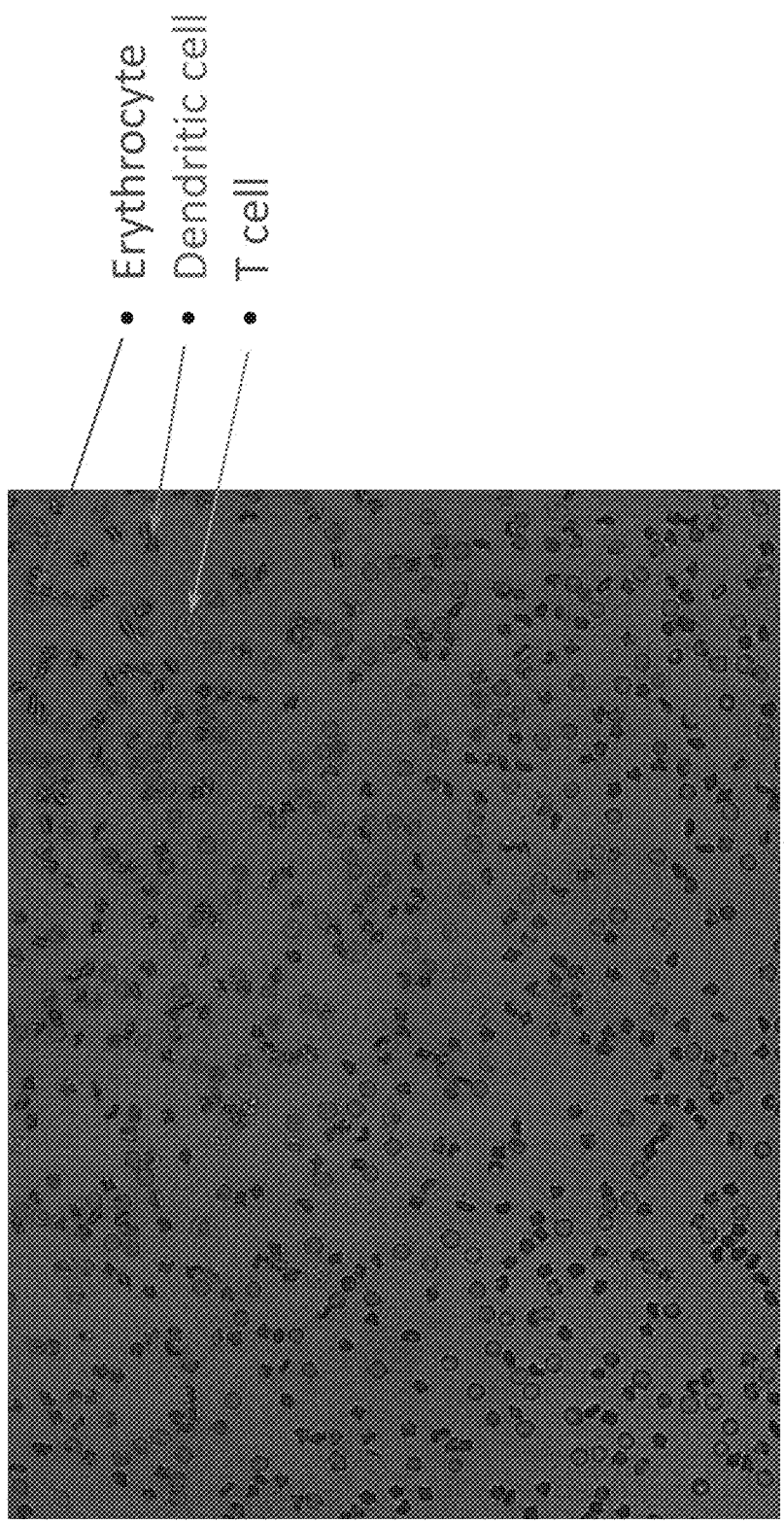
FIG. 13 is a microphotograph of a cell suspension with identification of an Erythrocyte, a Dendritic cell and a T cell.

The functionality of streptavidin-beads & biotin-beads was evaluated. Referring to FIGS. 10-12, streptevidin-conjugated and biotin-conjugated beads are shown to form complexes with each other, as expected, upon mixing, It may be desirable to obtain independent isolation of CD4+ and CD8+ ("helper" and "killer" T cells, respectively) from suspensions and mixing them in desired ratios with a view toward efficient therapy. Toward this end, acoustic beads with affinity for CD4 and CD8 receptors can be provided. A trial to obtain an example was performed with cell suspensions prepared from mice spleens. Referring to FIG. 13, identification of an Erythrocyte, a Dendritic cell and a T cell is provided. About 20 million (M) and 18M CD4+ and CD8+ T-cells, respectively, have been isolated from 4 spleens using Invitrogen depletion kits. Both cell lines can grow, and both CD4 and CD8 T-cells are about 8.2-8.6 µm.

Figure 15:
FIG. 15 is a microphotograph of a bright field image of green fluorescence of anti-CD4 antibodies bound to cells.
Figure 14:
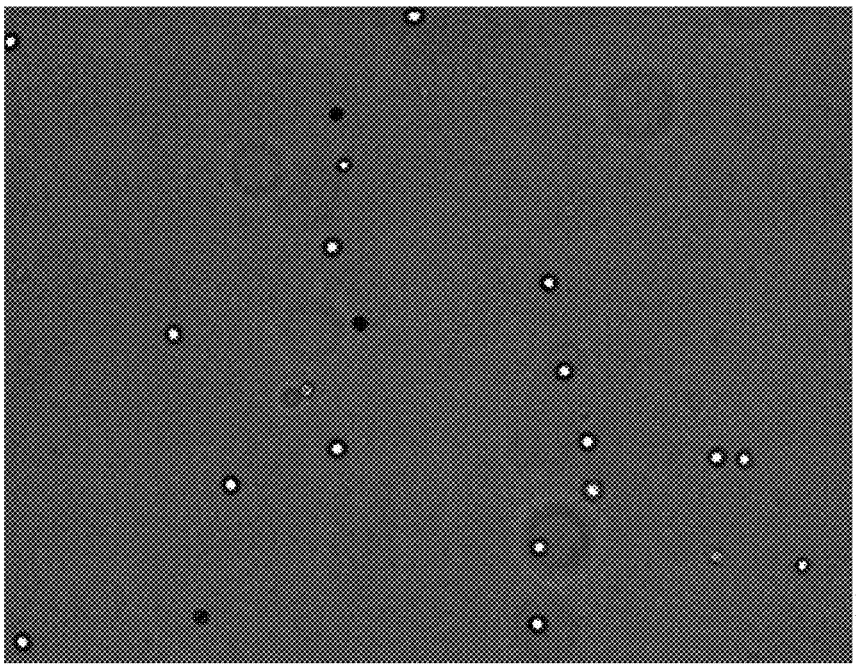
FIG. 14 is a microphotograph of a bright field image of cells.
Figure 16:
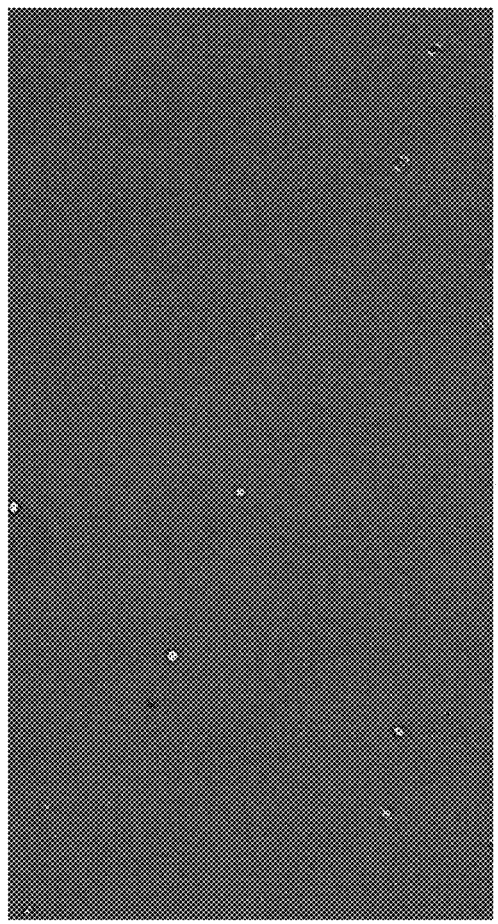
FIG. 16 is a microphotograph of a bright field image of cells.
Figure 17:
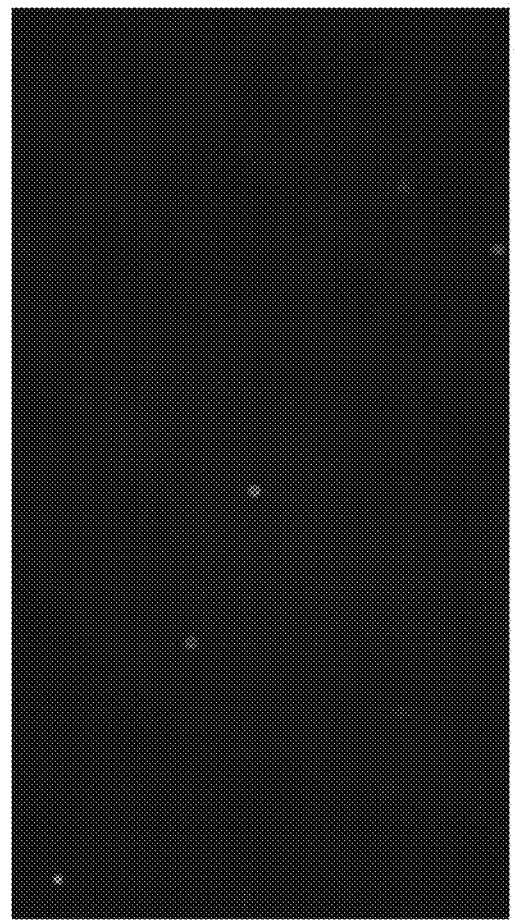
FIG. 17 is a microphotograph of a bright field image of magenta fluorescence of anti-CD4 antibodies bound to cells.

In this trial, CD4+ and CD8+ isolated cells were verified immunologically. Referring to FIGS. 14 and 15, verification of the presence of CD4 receptors is obtained. Alexa488 anti-CD4 antibodies are used to estimate the amount of isolated CD4 T-cells after purification from mouse spleens. FIG. 14 shows a bright field image with small circles being the cells in focal plane. FIG. 15 shows fluorescence of anti-CD4 antibodies bound to the cells. FIG. 16 shows a bright field image with small circles being the cells in focal plane. FIG. 17 shows fluorescence of anti-CD4 antibodies bound to the cells. The different colors of green and magenta in FIGS. 15 and 17, respectively, can allow multiplex analysis of results, e.g., a CD4/CD8 ratio.

Figure 18:
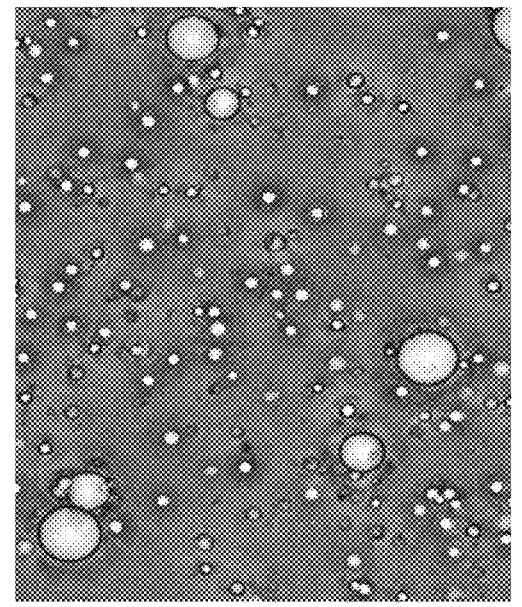
FIG. 18 is a series of microphotographs illustrate examples of bead-cell complexes in environments with an excess of beads and with an excess of cells.
Figure 18:
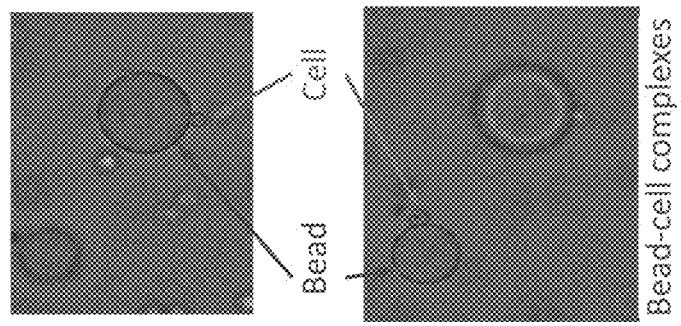
Figure 18:
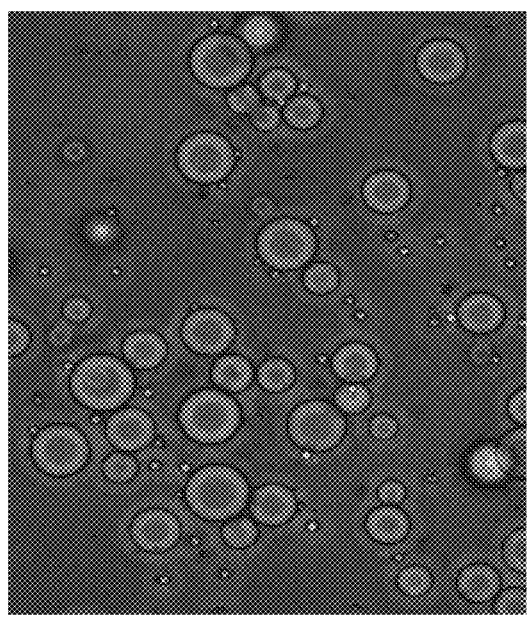

Referring now to FIG. 18, results of the trial are shown where Streptavidin-conjugated agarose beads were employed with biotin-conjugated anti-CD3 antibodies and CD3+ Jurkat T-cells. The affinity combinations of beads and cells is clearly illustrated. The beads can be separated out in an acoustic field to extract the cells from the mixture.

Proof-of-concept and validation of performance has been shown using acoustic affinity beads in an acoustic system. The disclosed methods and systems permit the use of off-shelf reagents, and currently available acoustic systems. The affinities can target any type of desired T cells or markers including CD3+, CD4+, CD8+. The acoustic beads can have a high, neutral or low contrast factor, which can affect how the beads respond to an acoustic field, for example being urged toward an acoustic node or antinode, or passing through the field.

The beads may be composed of various materials and combinations, which permits development of optimal chemistry with acoustic performance and biocompatibility. Some examples of bead constructs are provided in U.S. patent application Ser. No. 16/208,512, filed Dec. 3, 2018, the entire disclosure of which is incorporated herein by reference. The beads may be processed for isolation, sorting or any other function useful in a separation process. When used with a tuned acoustic system, the performance of specifically designed acoustic beads can match or exceed that of paramagnetic beads.

Existing chemistries may be used with the acoustic beads, and in conjunction with specifications of size and structure homogeneity to achieve desired results for acoustic and for isolation performance. The beads may be composed of composite constructs to advance acoustic efficiency. The acoustic system provides flexibility to manage small sizes, with heat management, and the use of fluidics to obtain results that are not possible with paramagnetic beads alone. The biocompatibility and/or biodegradability of the acoustic beads and simplified processing permits integration with existing hardware for CAR T cell manufacturing. The affinity acoustic beads can be used in a number of environments, including model environments such as, e.g., animal blood spiked with target cells and murine spleen extracts. The acoustic beads may thus be used in collaboration with existing systems, and may be designed and manufactured for target applications. The beads may be provided with a core that is acoustically active or neutral, and the bead themselves may be configured for high, neutral or low acoustic contrast. The size of the beads may be configured for separation and affinity in combination, for example a certain sized bead may include functionalized material to target a certain biomaterial, while another sized bead, may be functionalized to target another biomaterial, each of which can be separated simultaneously and continuously in a closed or flowing system. The beads can be designed to be of a homogeneous size distribution within a narrow or relatively broad range. Various affinity chemistries may be used, including streptavidin-biotin complex and immunoglobulin or aptamer. The beads may be designed for ease of manufacturability and/or for shelf-life. The beads may be used with approved chemistries, so that they may readily be integrated into known systems that use approved chemistries.

Figure 19:
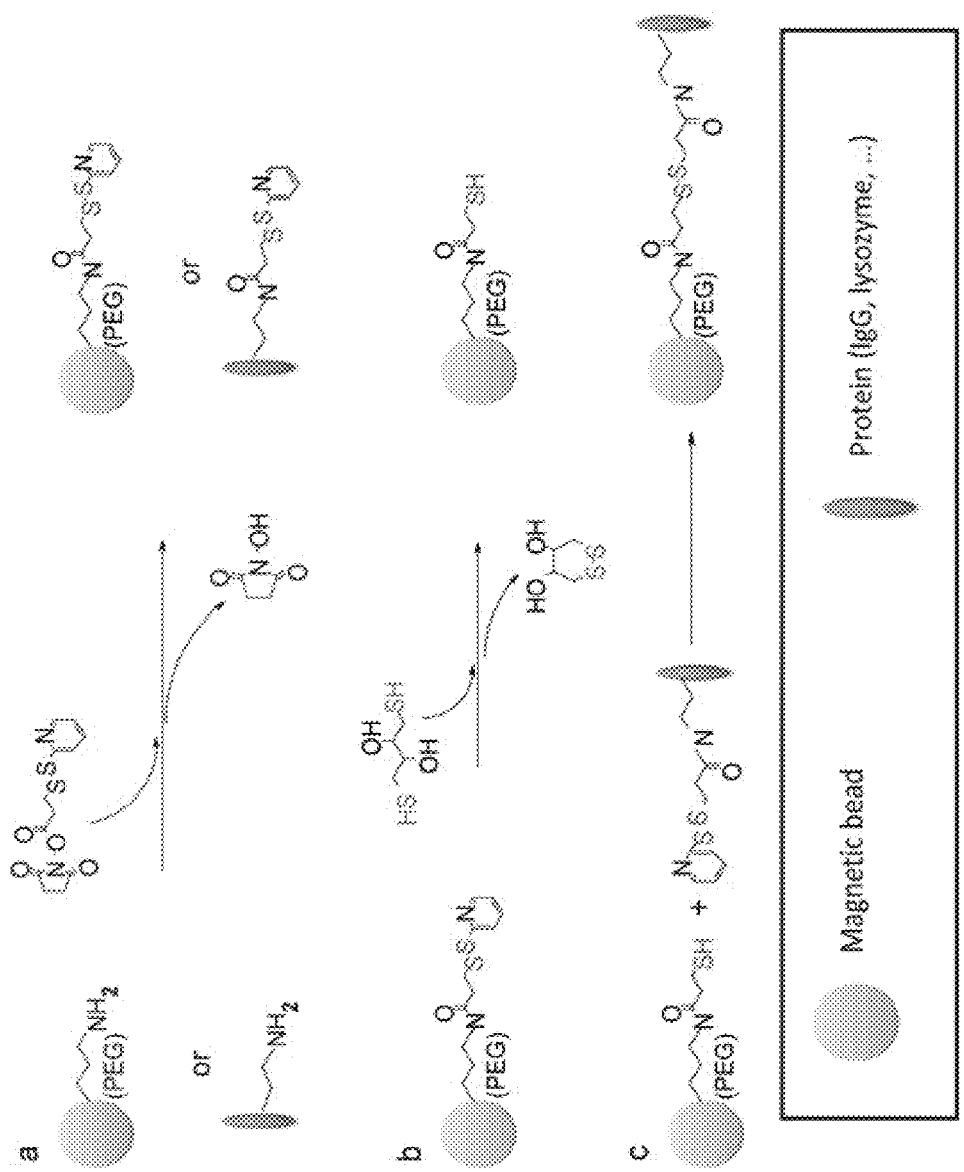
FIG. 19 is a diagram of example activation chemistries for affinity binding.

Referring to FIG. 19, an illustration of example activation chemistries is shown. The activation chemistries illustrated are applicable to the acoustic affinity beads described herein.

Figure 20:
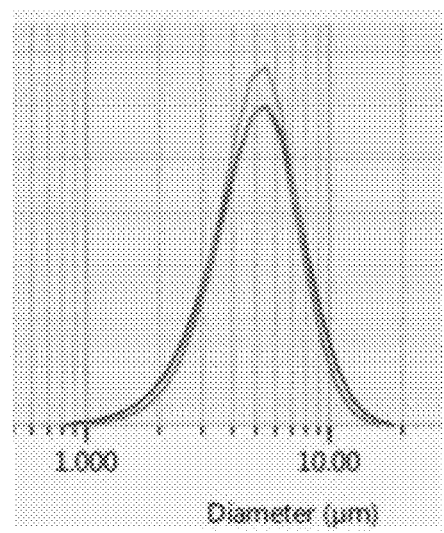
FIG. 20 is a graph showing bead size distribution with acoustic angled wave selection.

Referring to FIG. 20, a graph illustrating a size distribution of separated particles is shown. The distribution range is relatively small or tight, indicating the efficacy of the separation technique using the acoustic angled wave device.

Figure 21:
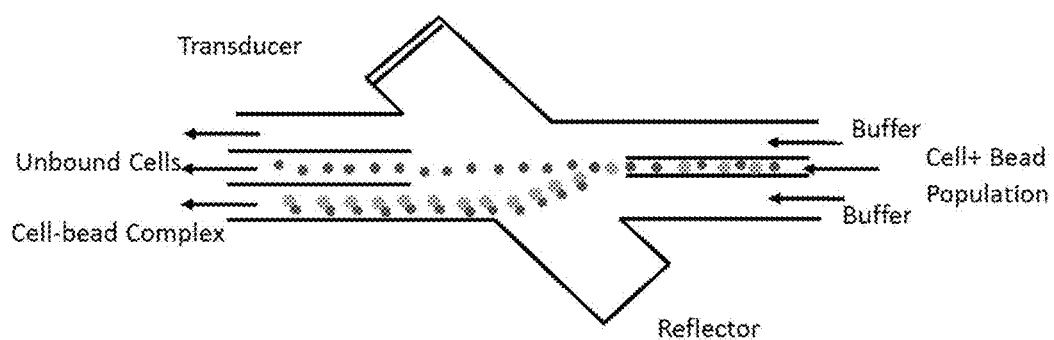
FIG. 21 is a diagram of an acoustic angled wave device showing bulk separation by size.

Referring to FIG. 21, a diagram of an operating mode of an acoustic angled wave device is illustrated. The larger size cell-bead complexes experience greater deflection passing through the angled acoustic wave than the cells alone, leading to the separation of the two populations. This technique can be applied in an affinity environment, where target material, such as specific cell types, bind to a functionalized bead to form a cell-bead complex that can be separated from the population using the acoustic angled wave device.

Figure 22:
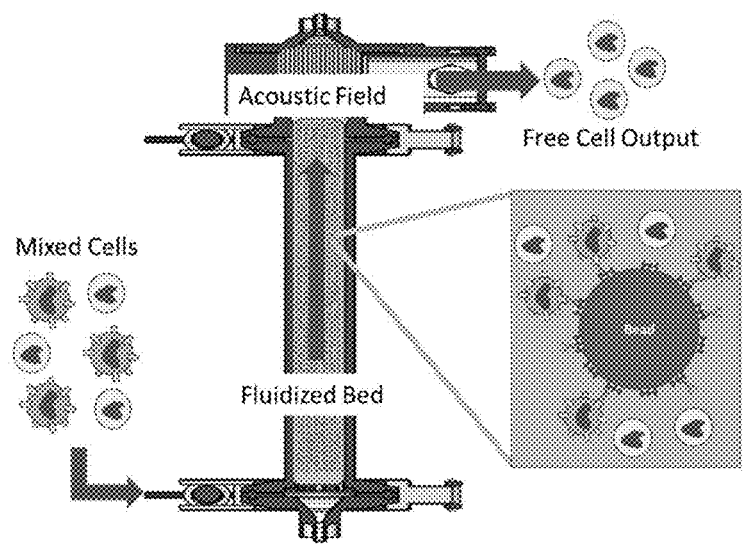
FIG. 22 is a diagram of an acoustic fluidized bed device for affinity cell selection.

Referring to FIG. 22, a diagram of an acoustic fluidized bed device is illustrated. The fluidized bed is composed of functionalized beads that bind to the target material as the target material is flowed through the fluidized bed. The beads are retained by the acoustic field in the column, thereby retaining in the column the target material attached to the beads. The bead-target material complexes are distinguished by the acoustic field from other materials flowed through the fluidized bed. The distinguishing characteristics may be dimensional, e.g. size or diameter, and/or may be based on acoustic contrast factor, density, compressibility, or any acoustically responsive characteristic that can differentiate components in the fluidized bed. The fluidized bed can be operated in a positive or negative selection mode, meaning that the desired product may be captured by attachment to the beads, or may be free to pass through the acoustic field to be recovered.

Figure 23:
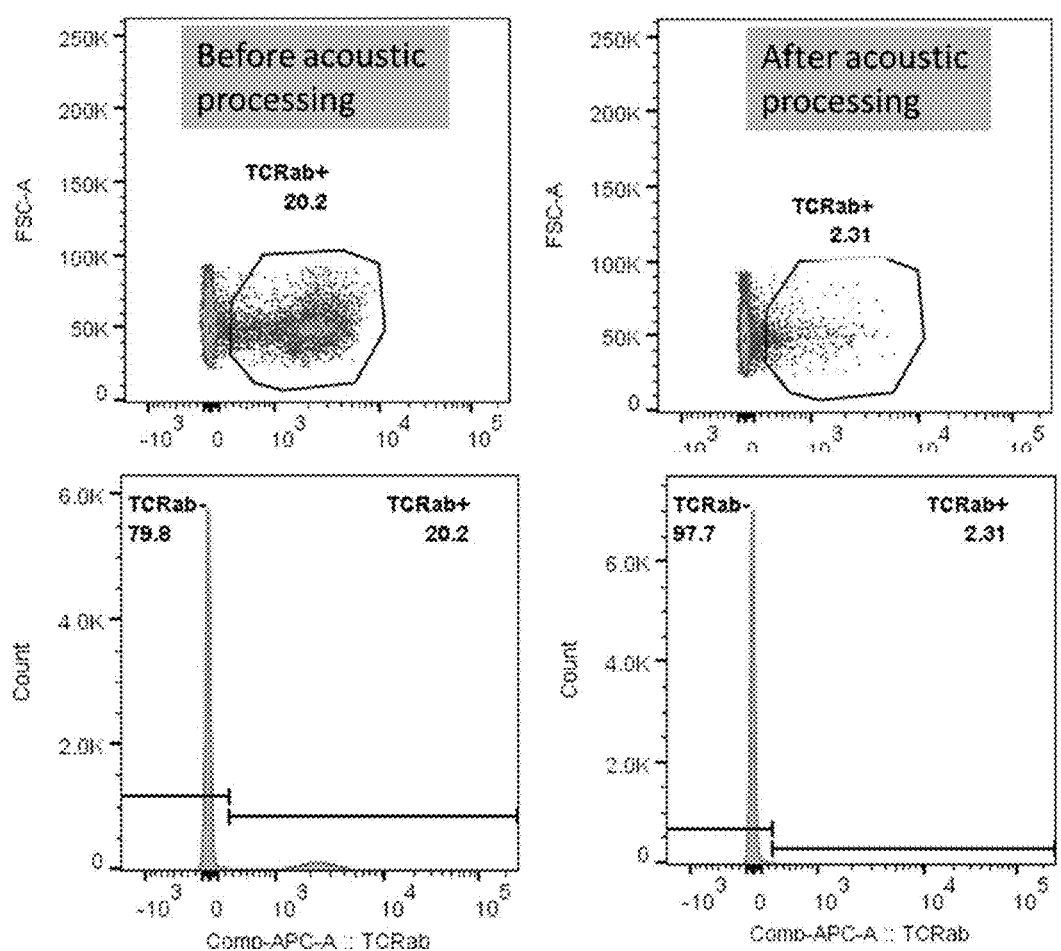
FIG. 23 is a set of graphs illustrating cytometer results from an acoustic affinity cell selection device.

Referring to FIG. 23, cytometer result graphs illustrate the efficacy of separation techniques using acoustic processing. In the example for the results illustrated in FIG. 23, TCR+ cells are removed from a mixed population of TCR+ and TCR– cells. As illustrated on the left-hand side graphs, the TCR+ population prior to acoustic processing is significant. The right-hand side graphs show a significant reduction in the TCR+ population following acoustic processing. The graphs illustrated in FIG. 23 are derived from an acoustic fluidized bed. Similar results are obtainable using an acoustic angled wave device.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the spirit of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

What is claimed is:

1. A method for separating biomaterial, comprising:
    applying a functionalized material to a plurality of beads that are free of ferro-magnetic material;
    suspending the beads in a fluid to obtain a bead suspension;
    exposing the bead suspension to biomaterial with an affinity for the functionalized material to permit the biomaterial to bind to the beads; and
    flowing the bead suspension in a chamber to an acoustic field generated in the chamber that traps the beads in the chamber against fluid flow.

2. The method of claim 1, further comprising:
    employing a column to house the bead suspension, such that a fluidized bed is formed with the bead suspension in the column; and
    retaining the beads in the column against fluid flow with the acoustic field.

3. The method of claim 1, further comprising:
    generating an angled acoustic wave at an oblique angle to a direction of fluid flow of the bead suspension; and
    deflecting the beads in the bead suspension away from a direction of fluid flow to permit separation of the beads from the fluid.

4. The method of claim 1, wherein the beads comprise acoustic beads.

5. The method of claim 1, wherein at least some of the plurality of beads are composed with an affinity for one or more of CD3, CD4 or CD8 receptors.

6. The method of claim 1, wherein the beads are one or more of biocompatible, biodegradable, or inert.

7. The method of claim 1, wherein the beads comprise one or more of agarose or a perfluorocarbon.

8. The method of claim 1, wherein the functionalized material is a streptavidin conjugate or a biotin conjugate.

9. The method of claim 1, wherein the beads comprise a liquid core and a lipid shell.

10. The method of claim 1, wherein the functionalized material includes affine molecules that are one or more of antibodies, aptamers or oligonucleotides.

11. The method of claim 1, wherein the functionalized material comprises a ligand.

12. The method of claim 1, further comprising reversing a binding between the biomaterial and the beads.

13. The method of claim 1, further comprising:
    isolating a first biomaterial and isolating a second biomaterial that is different from the first biomaterial; and
    combining the first biomaterial and the second biomaterial in a predetermined ratio.

14. The method of claim 1, wherein the beads further comprise at least two different sizes of beads, each size being configured with an affinity for a different type of biomaterial.

* * * * *